(12) United States Patent
Emmenegger et al.

(10) Patent No.: US 9,970,864 B2
(45) Date of Patent: May 15, 2018

(54) METHOD OF DETECTING A PROPELLANT GAS

(75) Inventors: Lukas Emmenegger, Dübendorf (CH); Jana Jágerská, Zürich (CH); Béla Tuzon, Dübendorf (CH)

(73) Assignee: WILCO AG, Wohlen (CH)

( * ) Notice: Subject to any disclaimer, the term of this patent is extended or adjusted under 35 U.S.C. 154(b) by 0 days. days.

(21) Appl. No.: 14/397,888

(22) PCT Filed: May 2, 2012

(86) PCT No.: PCT/EP2012/058041
§ 371 (c)(1),
(2), (4) Date: Oct. 30, 2014

(87) PCT Pub. No.: WO2012/107597
PCT Pub. Date: Aug. 16, 2012

(65) Prior Publication Data
US 2015/0083918 A1 Mar. 26, 2015

(51) Int. Cl.
| | | |
|---|---|---|
| *G01J 5/02* | (2006.01) | |
| *G01N 21/3504* | (2014.01) | |
| *G01M 3/22* | (2006.01) | |
| *G01M 3/38* | (2006.01) | |
| *G01N 33/00* | (2006.01) | |
| *G01N 21/03* | (2006.01) | |

(52) U.S. Cl.
CPC ........ *G01N 21/3504* (2013.01); *G01M 3/226* (2013.01); *G01M 3/38* (2013.01); *G01N 33/0036* (2013.01); *G01N 21/031* (2013.01); *G01N 2201/0697* (2013.01); *G01N 2201/0698* (2013.01); *G01N 2201/06113* (2013.01)

(58) Field of Classification Search
CPC .. G01N 21/3581; G01N 21/35; G01N 21/359; G01N 21/4795; G01J 3/42
See application file for complete search history.

(56) References Cited

U.S. PATENT DOCUMENTS 3,460,910 A * 8/1969 Emich ............................. 422/54
5,379,115 A * 1/1995 Tsai .................... G01B 9/02019
356/487
(Continued)

FOREIGN PATENT DOCUMENTS

EP 0791814 8/1997

OTHER PUBLICATIONS

International Preliminary Report and Written Opinion for Application No. PCT/EP2012/058041, filed May 2, 2012.
(Continued)

*Primary Examiner* — David Porta
*Assistant Examiner* — Mamadou Faye
(74) *Attorney, Agent, or Firm* — Oliff PLC

(57) ABSTRACT

A method and a system for detecting the presence of propellant gas in a gaseous sample exploit laser light especially in the 3.30-3.5 μm range. The propellant can be propane, n-butane, i-butane, dimethyl ether, methyl ethyl ether, HFA 134a, HFA 227, or any other propellant exhibiting absorption in the requisite wavelength range. The presence of the application of this method in leak testing of propellant-containing containers such as aerosols or fuel canisters, permits high-speed, high accuracy leak detection capable of replacing existing testing methods.

55 Claims, 14 Drawing Sheets

(56) References Cited

U.S. PATENT DOCUMENTS

| | | | |
|---|---|---|---|
| 5,388,446 A * | 2/1995 | Kronberg | 73/40.7 |
| 6,302,105 B1 * | 10/2001 | Wickham et al. | 128/204.18 |
| 6,969,357 B1 * | 11/2005 | Colman et al. | 600/529 |
| 7,154,103 B2 * | 12/2006 | Koenck et al. | 250/455.11 |
| 8,591,826 B2 * | 11/2013 | Auer et al. | 422/300 |
| 2004/0007904 A1 * | 1/2004 | Lin et al. | 297/184.1 |
| 2007/0121689 A1 * | 5/2007 | Brown | 372/39 |
| 2007/0240493 A1 * | 10/2007 | Conlan et al. | 73/40.7 |
| 2008/0112787 A1 * | 5/2008 | Rebstock | 414/749.1 |
| 2010/0034669 A1 * | 2/2010 | Imholt | B82Y 30/00 417/51 |
| 2010/0053605 A1 * | 3/2010 | Ragucci | G01N 21/3504 356/301 |
| 2010/0326169 A1 * | 12/2010 | Grosse-Bley et al. | 73/31.05 |
| 2011/0031402 A1 * | 2/2011 | Huttmann | G01N 21/03 250/340 |
| 2011/0132063 A1 * | 6/2011 | Wang et al. | 73/1.03 |
| 2015/0185144 A1 * | 7/2015 | Hirata | G01N 21/39 356/437 |

OTHER PUBLICATIONS

Written Opinion and International Search Report for Application No. PCT/EP2012/058041, filed Feb. 5, 2012.

N. Kasai, et al.; "Propane gas leak detection by infrared absorption using carbon infrared emitter and infrared camera", NDT&E International, Butterworth—Heinemann, Oxford, GB, vol. 44, No. 1, Jan. 1, 2011, pp. 57-60.

* cited by examiner

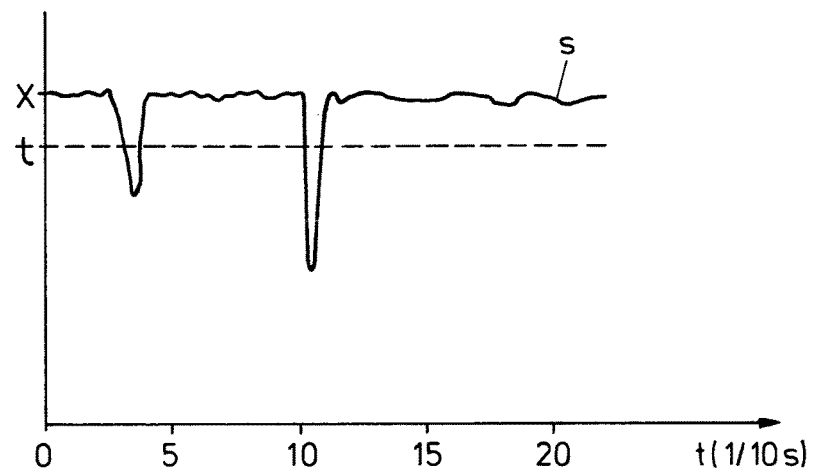
FIG. 11
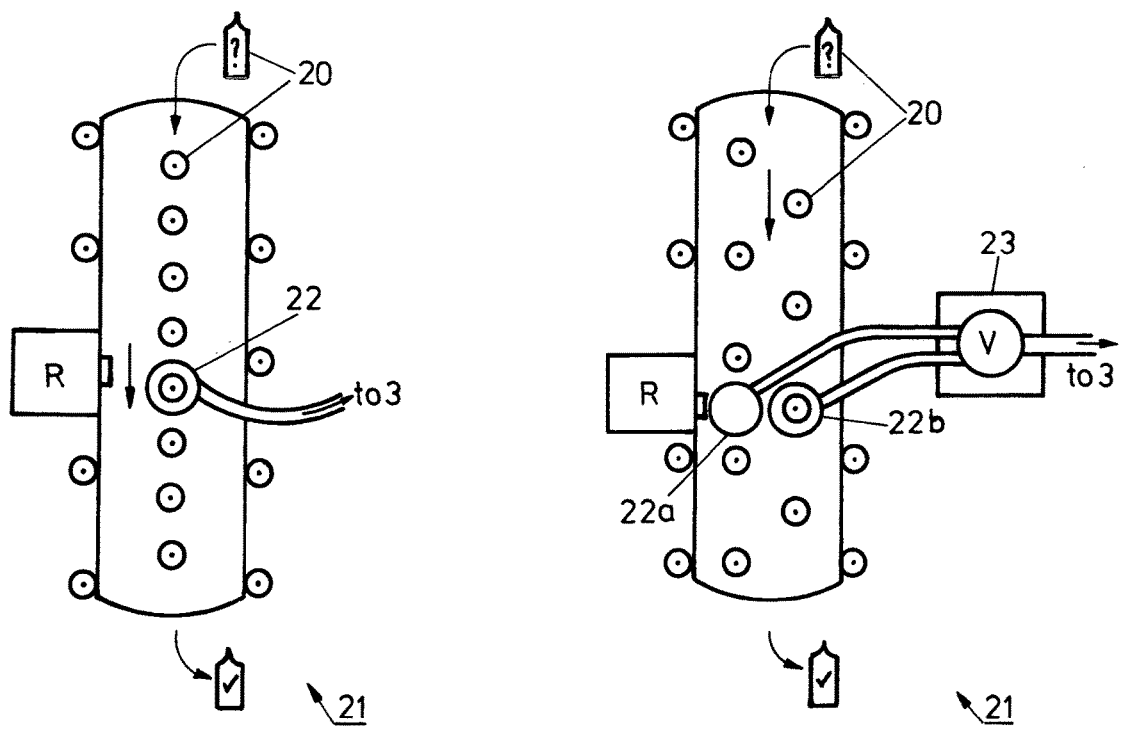
FIG. 12
FIG. 13

METHOD OF DETECTING A PROPELLANT GAS

RELATED APPLICATION

This application is a U.S. national phase application of International Application number PCT/EP2012/058041 filed May 2, 2012.

TECHNICAL FIELD

The present invention relates to a method of detecting certain propellant gases in a gaseous sample, with particular but not exclusive application in the leak testing of containers, such as of aerosol cans or of fuel canisters containing e.g. propane and/or butane.

BACKGROUND

Propellant gases are required to have certain properties: they must be gaseous in the anticipated range of temperatures in which they are to be used, particularly around room temperature, and they must be liquid under a pressure which permits the use of lightweight disposable containers, i.e. the pressure required is insufficient to cause the container to burst at the highest temperature likely to be experienced by the container in normal use. They must also be economic to use. As a result, amongst the most commonly used propellants today are propane, n-butane, i-butane, dimethyl ether, methyl ethyl ether, HFA 134a (1,1,1,2-tetrafluoroethane), and HFA 227 (1,1,1,2,3,3,3-heptafluoropropane), the latter two having particular application in the medical field for aerosol inhalers. In the present specification, when not otherwise stated, "butane" refers to either isomer, or any mixture of both isomers of butane.

Under current regulations, every single propellant containing container, such as aerosols or propane and/or butane fuel Containers (which Contain propane and/or butane as both product and propellant), must be tested for leakage during production. The standard method is based on a hot water bath, as described in the aerosol dispensers directive 2008/47/EC. This process is extremely costly in terms of equipment, energy, and labour, since it requires a large water bath (±/−20,000 L) to be maintained at a temperature of 50° C., and an operator must watch for bubble formation and manually reject any leaking containers. Each operator is limited to a testing rate of about 60 units per minute, and the possibility for human error is high. In addition, a large amount of waste water contaminated with leaking products from the aerosol cans is produced.

Several alternatives to the water bath method have been developed.

The first of these is a detection method based on pressure change detection, developed by the Applicant, for leak testing the crimp and valve of filled aerosol cans. This system was designed to meet the specifications given in UN/SCETDC/INF.93, that is to say it is capable of detecting leak rates of $2.0 \times 10^{-3}$ mbar 1 s$^{-1}$. Cans are placed onto a continuously moving carousel, and test chambers are then lowered over the top of the aerosol cans, hermetically sealing the crimp and valve section. Subsequently, a slight overpressure is created in the test chamber, and any leakage of the can causes a pressure change in the test chamber which is then detected. However, current versions of the system are limited in throughput since the pressure change detection is relatively slow, thus multiple units in parallel are required to achieve high production speed, which is commonly demanded at the 500 per minute level. This level of throughput requires approximately 60 test chambers.

A second alternative to the water bath is based on the principle of flame ionisation detection. This method is however slow, and the testing rate is currently limited to approximately 50-100 containers per minute, requiring between 5 and 10 costly detectors in parallel to achieve a 500 per minute test rate. In addition, due to safety and cost considerations, the presence of a flame in the context of propane/butane leak detection is undesirable.

A third alternative to the water bath is provided by an optical test method based on quantum cascade lasers in the 7.2 μm frequency range. The lasers are arranged to chirp so as to provide a frequency-range scan, and the received signal is subject to digitised spectrum analysis to identify the spectroscopic peaks in a sample captured from around an aerosol can. To do this, a processor runs a fitting algorithm over the spectrum produced by the sample of gas that has been captured to determine whether or not butane or propane is present. However, since this frequency analysis is carried out in the 7.2 μm range, the propellant absorption spectra overlap that of water, which reduces the precision of the analysis and requires significant computing power to perform, since spectral analysis of the received laser light is a computationally-heavy method per se.

DISCLOSURE OF INVENTION

The object of the invention is therefore to overcome at least one of the above-mentioned disadvantages, and thereby to propose a method of detecting at least one of the above-mentioned propellant gases in a gaseous sample which is faster, and/or more accurate, and/or more economic than existing methods, and/or is capable of replacing existing water bath methods.

This object is achieved by a method of detecting the presence of at least one propellant gas in a gaseous sample, by receiving the sample in a sample chamber, generating test laser light pulses and reference laser light pulses with a spectrum of the laser light at least partially situated within the spectrum range wherein absorption is indicative for the presence of said propellant gas, especially in the range of 3.30-3.55 μm, passing at least the test laser light pulses through the sample chamber, detecting both the test laser light pulses and the reference laser light pulses by at least one detector, and comparing, e.g. by considering the difference or the ratio, the amplitude of at least one detected test laser light pulse with the amplitude of at least one detected reference light pulse, and thereby determining the presence or absence of propellant above a threshold concentration in the sample chamber, e.g. by determining whether the ratio or difference of the amplitude of the test and reference laser light pulses is above or below a particular predetermined threshold value. This method in the 3.30-3.55 μm range can detect most of today's commonly used propellants, namely propane, n-butane, i-butane, dimethyl ether, methyl ethyl ether, HFA 134a, HFA 227, and any other propellants exhibiting absorption in the wavelength range of the laser used. In fact, any propellant gas having at least one C—H bond in its molecular structure is believed to exhibit absorption in the requisite range. Propellants that cannot be detected by this method include nitrous oxide, carbon dioxide, CFC11 and CFC12, since they do not exhibit absorption in the 3.30-3.55 μm range. Exploiting the addressed spectral range is particularly advantageous, since water (vapour) substantially does not absorb light energy in this range, which leads to more accurate results. Furthermore, by simply comparing amplitudes of received laser light pulses, there is no requirement for the laser light to sweep a frequency range. Simply comparing amplitudes significantly simplifies the method compared to prior art optical methods.

In an embodiment, which may be combined with any subsequently or previously addressed embodiment, unless in contradiction, the test laser light pulses and the reference laser light pulses are generated by beam splitting pulsed laser light from a single laser source. This permits the use of a single laser source, reducing the number of components, and eliminating the necessity for calibration of the laser source.

In an embodiment, which may be combined with any subsequently or previously addressed embodiment, unless in contradiction, the test laser light pulses and the reference laser light pulses are generated by first and second laser light sources respectively. This permits flexibility in component layout and optical path architecture.

In an embodiment, which may be combined with any subsequently or previously addressed embodiment, unless in contradiction, the test laser light pulses and the reference laser light pulses are detected by the same, single, detector. This reduces the number of components and eliminates the necessity for calibration of multiple detectors.

In an embodiment, which may be combined with any subsequently or previously addressed embodiment, unless in contradiction, the test laser light pulses and the reference laser light pulses are detected by first and second detectors respectively. This permits flexibility in component layout and optical path architecture.

In an embodiment, which may be combined with any subsequently or previously addressed embodiment, unless in contradiction, the sample chamber is a multipass chamber and the test laser light pulses travel through the sample chamber in a plurality of passes. This increases the measurement accuracy by exposing the laser light to a greater amount of propellant and thus achieving greater absorption than is possible with a single pass chamber of reasonable extent.

In an embodiment, which may be combined with any subsequently or previously addressed embodiment, unless in contradiction, the optical path in ambient air travelled by the test laser light pulses is substantially equal to the optical path in ambient air travelled by the reference laser light pulses, except for the path through the sample chamber. This ensures that both the test laser light pulses and the reference laser light pulses are e.g. exposed to the same amount of ambient air, the same attenuation from optical components e.g. mirrors, and are thus subjected to the same attenuation and introduction of noise. This improves the measurement accuracy by ensuring that there is no differential interference between the test and the reference laser light pulses.

In an embodiment, which may be combined with any subsequently or previously addressed embodiment, unless in contradiction, the total optical path travelled by the test laser light pulses is different to the total optical path travelled by the reference laser light pulses. This enables the test and reference laser light pulses to be received time-shifted with respect to one another and thus be distinguished easily at the one or more than one detectors. In a good embodiment, the path difference is the path through the sample chamber.

In an embodiment, which may be combined with any subsequently or previously addressed embodiment, unless in contradiction, the difference in optical paths travelled by the test and by the reference laser light pulses is such that the time separation of the pulses at the at least one detector is greater than 100 ns. This ensures that the detected test and reference laser light pulses do not overlap and interfere. In practice, 120 ns has shown to give excellent results.

In an embodiment, which may be combined with any subsequently or previously addressed embodiment, unless in contradiction, the reference laser light pulses bypass the sample chamber. This results in a high signal-to-noise ratio and reliable results.

In an embodiment, which may be combined with any subsequently or previously addressed embodiment, unless in contradiction, the reference laser light pulses are generated when there is known to be substantially no propellant in the sample chamber, and the reference laser light pulses are also passed through the sample chamber. This gives a particularly simple and robust construction of optical path architecture.

In an embodiment, which may be combined with any subsequently or previously addressed embodiment, unless in contradiction, the laser light pulses are generated by a Vertical External Cavity Surface Emitting Laser (VECSEL) or a Quantum Cascade Laser (QCL). These are two known examples of types of laser capable of operating in the wavelength range of 3.30-3.55 μm, the VECSEL being available from Phocone AG and the QCL from Alpes Laser AG.

In an embodiment, which may be combined with any subsequently or previously addressed embodiment, unless in contradiction, the laser light pulses are generated at a repetition rate of 5-15 kHz, or 7-13 kHz, or 9-11 kHz, or substantially at 10 kHz. This gives a repetition rate high enough to give a good degree of over-sampling for measurement accuracy, without being so high as to require excessively high-frequency optical and/or electrical processing.

In an embodiment, which may be combined with any subsequently or previously addressed embodiment, unless in contradiction, the laser light pulse duration is between 5-15 ns, or 7-13 ns, or 9-11 ns, or substantially of 10 ns. These ranges have proven to give good results.

In an embodiment, which may be combined with any subsequently or previously addressed embodiment, unless in contradiction, the sample is flown continuously into and out of the sample chamber by being drawn by a pump operating at a predetermined substantially constant flow rate.

This pump can be of any known type such as a centrifugal pump, an axial flow pump, a Venturi pump (which runs on compressed air thus is vibration free). The constant flow rate through the sample chamber prevents vibration in the system due to variations in flow velocity of the pump, which is particularly advantageous in the case of a multipass sample chamber being used, since these can be sensitive to such pneumatic and/or mechanical vibration.

In an embodiment, which may be combined with any subsequently or previously addressed embodiment, unless in contradiction, the sample chamber and pump are arranged so as to provide a pressure in the sample chamber of between 10 mbara and 1000 mbara, or between 50 mbara and 150 mbara, or substantially 100 mbara. This enables a pressure to be selected which balances the requirements for measurement accuracy (higher pressure thus a higher partial pressure of propellant in the sample chamber) and measurement speed (low pressure, thus a higher rate of gas flow)

The invention is further directed to a method of leak testing containers containing at least one propellant. The method comprises obtaining a gaseous sample from the surroundings of a container, and testing the sample according to one of the above disclosed methods of detecting the presence of propellant gas in a gaseous sample. By surroundings we understand the volume immediately adjacent to the container, particularly to the valve and crimp area. This should be less than 10 cm distant from the container, or less than 7 cm therefrom, or less than 5 cm therefrom, or less than 3 cm therefrom, or less than or 2 cm therefrom.

In an embodiment of a method of leak testing containers, which may be combined with any subsequently addressed embodiment of a method of leak testing containers, unless in contradiction, the gaseous sample is taken from the surroundings of the container by means of a sniffer, which may be a sniffer cup, a portal-type arrangement, a pre-chamber placed over the container, or any other conceivable arrangement.

In an embodiment of a method of leak testing containers, which may be combined with any subsequently or previously addressed embodiment of a method of leak testing containers, unless in contradiction, the gaseous sample is drawn into the sniffer at a substantially constant flow rate by means of a suction pump. This pump can be of any known types such as a centrifugal pump, an axial flow pump, a Venturi pump (which runs on compressed air or water thus is vibration free). The constant flow rate prevents vibration in the system and oscillation in the gaseous sample, which is particularly advantageous in the case of a multipass sample chamber being used, since these can be sensitive to vibration and gas-stream pulsating in the sample chamber.

In an embodiment of a method of leak testing containers, which may be combined with any subsequently or previously addressed embodiment of a method of leak testing containers, unless in contradiction, the suction pump is situated downstream of the sample chamber, which reduces gas stream pulsating in the sample chamber and improves consistency of flowrate.

In an embodiment of a method of leak testing containers, which may be combined with any subsequently or previously addressed embodiment of a method of leak testing containers, unless in contradiction, a plurality of containers are tested in line, i.e. sequentially. This enables high-speed serial leak testing of containers.

In an embodiment of a method of leak testing containers, which may be combined with any subsequently or previously addressed embodiment of a method of leak testing containers, unless in contradiction, the plurality of containers are conveyed sequentially past a sniffer, resulting in a simple testing arrangement which has been shown in practice to achieve at least 600 tested containers per minute.

In an embodiment of a method of leak testing containers, which may be combined with any subsequently or previously addressed embodiment of a method of leak testing containers, unless in contradiction, the plurality of containers are conveyed sequentially and alternately past at least a pair of sniffers, i.e. one container past the first sniffer, the next container past the other sniffer, the next container past the first sniffer, and so on, potentially enabling a higher testing rate.

In an embodiment of a method of leak testing containers, which may be combined with any subsequently or previously addressed embodiment of a method of leak testing containers, unless in contradiction, each sniffer is brought into fluid connection with the sample chamber in turn as a container is conveyed past the respective sniffer. This prevents cross contamination of samples from each sniffer (i.e. from previous and/or subsequent containers), and prevents dilution of the sample from the sniffer not in proximity to a container at that moment. Advantageously, a crossover valve connects each sniffer in turn to the sample chamber while ensuring a substantially constant flowrate into the sample chamber, which prevents changes in the flowrate from causing vibrations and gas-stream pulsating, which may adversely affect a multipass sample chamber. In both modes of conveyance, the conveying may be carried out either linearly, or on a curve or e.g. by rotary conveyance.

In an embodiment of a method of leak testing containers, which may be combined with any subsequently or previously addressed embodiment to a method of leak testing containers, unless in contradiction, the surroundings of the container from which the gaseous sample is taken are purged with clean air, e.g. air taken from an uncontaminated environment such as outdoors, or other clean gas, e.g. nitrogen, argon etc, before the sample is taken. This reduces contamination of the testing environment due to e.g. polluted ambient air containing amounts of propellant in the building in which the method is being carried out. By reducing this contamination, the accuracy of the method can be improved.

In an embodiment of a method of leak testing containers, which may be combined with any subsequently or previously addressed embodiment, unless in contradiction, the surroundings and surface to the container are purged by passing the container through at least one air curtain. This is a simple way to realise the above-mentioned purging.

In an embodiment of a method of leak testing containers, which may be combined with any subsequently or previously addressed embodiment of a method of leak testing containers, unless in contradiction, the air curtain defines an entrance to an isolation chamber, a further air curtain being provided and defining the exit of said isolation chamber, the gaseous sample being obtained from the surroundings of the container when said container is within said isolation chamber. This further isolates the testing environment from the ambient air and any contamination it contains, thus improving detection accuracy.

In an embodiment of a method of leak testing containers, which may be combined with any subsequently or previously addressed embodiment of a method of leak testing containers, unless in contradiction, clean air or other clean gas is introduced into an upper portion, i.e. the top, of said isolation chamber, such as by pumping it in, so as to generate a top-to-bottom flow of air or gas in said isolation chamber. This helps to purge the inside of the isolation chamber of any propellant which has been introduced into it e.g. by a leaky container. Since the propellants in question are denser than air, they will naturally tend to sink to the bottom of the chamber, and a degree of air forcing speeds up this process, thus assisting in improving measurement accuracy.

In an embodiment of a method of leak testing containers, which may be combined with any subsequently or previously addressed embodiment of a method of leak testing containers, unless in contradiction, air or other gas in the isolation chamber is extracted actively, passively, or both actively and passively, in a lower portion of the isolation chamber. This further assists in purging the isolation chamber, thus ensuring that any propellant contamination therein is quickly extracted.

In an embodiment of a method of leak testing containers, which may be combined with any subsequently or previously addressed embodiment of a method of leak testing containers, unless in contradiction, the gaseous sample is taken from the surrounding of the container by means of a pre-chamber. This pre-chamber enables a build-up of leaking propellant in its interior, thus increasing the concentration of leaking propellant sampled compared with merely passing containers past a sniffer. This improves the detection accuracy, and also helps isolate the container being tested from the surrounding environment, which is advantageous in the case when the surrounding environment is contaminated with propellant.

In an embodiment of a method of leak testing containers, which may be combined with any subsequently or previously addressed embodiment of a method of leak testing containers, unless in contradiction, the pre-chamber is purged with clean air or other clean gas before the sample is taken. This ensures that any contaminated air or propellant contained within the pre-chamber is flushed and thereby cleaned so that any possible contamination that was in the pre-chamber is removed before the sample is taken, and thus cannot affect the detection accuracy. This purging can be performed by flushing the pre-chamber before the container is present therein, and/or once the container is present therein.

In an embodiment of a method of leak testing containers, which may be combined with any subsequently or previously addressed embodiment of a method of leak testing containers, unless in contradiction, the sample is taken by passing the pre-chamber past a snifter. This gives a simple construction which nevertheless has improved detection accuracy compared to merely passing containers past a snifter, since the concentration of propellant in the interior of the pre-chamber due to a leaking container will be greater than the concentration o~ propellant around a leaking container in free air.

In an embodiment of a method of leak testing containers, which may be combined with any subsequently or previously addressed embodiment of a method of leak testing containers, unless in contradiction, the sample is taken by bringing the interior of the pre-chamber into connection with the sample chamber. This results in improved detection accuracy, since the concentration of propellant that has built up in the pre-chamber will be directly drawn into the sample chamber, thus increasing the concentration of propellant therein compared with passing containers or pre-chambers past a snifter: essentially, the pre-chamber in this embodiment can be considered as forming at least part of the snifter. To speed up the process of drawing the samples in, vacuum means may be provided to assist therewith.

The invention further directed to a method of manufacturing leak tested containers containing at least one propellant gas, comprising manufacturing filled and untested containers, leak testing the containers according to one of the above-mentioned methods, rejecting the container from the surroundings of which the gaseous sample was taken, i.e. the container being tested (i.e. under test), and if propellant gas is detected in the sample chamber above a predefined threshold concentration, accepting the container from the surroundings of which the gaseous sample was taken (i.e. the container under test) as leak tested if less than the threshold concentration of propellant is detected in the sample chamber, which naturally incorporates the case of no propellant being detected.

Alternatively, the method of manufacturing leak tested containers can comprise manufacturing filled, untested containers, subjecting the containers to a coarse leak detection test, containers failing this coarse leak detection test being rejected, then subsequently leak-testing containers not rejected based on the results of the course leak detection test according to any of the leak testing methods described above, rejecting the container from the surroundings of which the gaseous sample was taken, i.e. the container currently being tested, if propellant gas is detected in the sample chamber as being above the predefined threshold concentration, and if said propellant gas is detected in the sample chamber below the predefined threshold concentration, which naturally incorporates the case in which no propellant is detected, accepting the container from the surroundings of which the gaseous sample was taken as an unleaky container. By this method, contamination of the testing environment for the (primary) leak testing method due to an extremely leaky container, i.e. one that is "blowing" propellant by rejecting such a heavily leaky container before it reaches the sensitive leak detection system.

In an embodiment, the coarse leak detection test comprises passing the container beneath a flap arranged to react to a predetermined threshold gas flow rate, detecting this reaction, and actuating a rejection mechanism based on this detection. This provides an extremely simple method for detecting a very leaky container.

Furthermore, the invention is directed to a propellant gas detector system comprising a sample chamber; a laser light generating arrangement with an output for reference laser light pulses and for test laser light pulses, said laser light having a spectrum at least partially situated in a spectral range wherein absorption is indicative for the presence of said propellant gas, especially in the range of 3.30 to 3.55 µm wavelength; a detector arrangement with a detector input for test laser light pulses and reference laser light pulses and with a detector output, said output of said laser light generating arrangement being operationally connected to said detector input via said sample chamber; a comparing processing unit with a processing input and a processing output; said detector output being operationally connected to said processing input; said comparing processing unit generating at said processing output a result signal of a comparison of the amplitude of the said test laser light pulses and the amplitude of the said reference laser light pulses applied to said processing input from said detector output.

This system operating in the 3.30-3.55 µm range can detect most of today's commonly used propellants, namely propane, n-butane, i-butane, dimethyl ether, methyl ethyl ether, HFA 134a, HFA 227, and any other propellants exhibiting absorption in the wavelength range of the laser used. In tact, any propellant gas having at least one C—H bond in its molecular structure is believed to exhibit absorption in the requisite range. Propellants that cannot be detected by this system include nitrous oxide, carbon dioxide, CFC11 and CFC12, since they do not exhibit absorption in the 3.30-3.55 µm range. Exploiting the addressed spectral range is particularly advantageous, since water (vapour) substantially does not absorb light energy in this range, which leads to more accurate results. Furthermore, by simply comparing amplitudes of received laser light pulses, there is no requirement for the laser light to sweep a frequency range. This simple comparison of amplitudes significantly simplifies the system compared to prior art optical systems.

In an embodiment of a propellant gas detector system, which may be combined with any previously or subsequently addressed embodiment of a propellant gas detector system, unless in contradiction, the laser light generating arrangement comprises a single laser source, and wherein a beam splitter is provided in operational connection with the single laser source and upstream of the input to the sample chamber. The beam splitter thus is arranged to split pulsed laser light from the single laser source into the previously addressed test laser light pulses and reference laser light pulses. This permits the use of a single laser source, reducing the number of components, and eliminating the necessity for calibration of the laser source.

In an embodiment of a propellant gas detector system, which may be combined with any previously or subsequently addressed embodiment of a propellant gas detector system, unless in contradiction, the laser generating arrangement comprises a first laser source for generating the test laser light pulses and a second laser source for generating the reference laser light pulses. This permits flexibility in component layout and optical path architecture.

In an embodiment of a propellant gas detector system, which may be combined with any previously or subsequently addressed embodiment of a propellant gas detector system, unless in contradiction, the detector arrangement comprises a single detector. This reduces the number of components and eliminates the necessity for calibration of multiple detectors.

In an embodiment of a propellant gas detector system, which may be combined with any previously or subsequently addressed embodiment of a propellant gas detector system, unless in contradiction, the detector arrangement comprises a first detector in operational connection with the output of said laser light generating arrangement and receiving test laser light pulses, and a second detector in operational connection with the output of said laser light generating arrangement and receiving reference laser light pulses. This permits flexibility in component layout and optical path architecture.

In an embodiment of a propellant gas detector system, which may be combined with any previously or subsequently addressed embodiment of a propellant gas detector system, unless in contradiction, the sample chamber is a multipass chamber. This increases the measurement accuracy by exposing the laser light to any propellant present in the chamber for a longer time and thus achieving greater absorption than is possible with a single pass chamber of reasonable extent.

In an embodiment of a propellant gas detector system, which may be combined with any previously or subsequently addressed embodiment of a propellant gas detector system, unless in contradiction, the optical path in ambient air for the test laser light pulses is substantially the same length as the optical path in ambient air for the reference laser light pulses, except for the path through the sample chamber. This ensures that both the test laser light pulses and the reference laser light pulses are exposed e.g. to the same amount of ambient air, and are thus subjected to the same attenuation and introduction of noise. This improves the measurement accuracy by ensuring that there is no differential interference between the test and the reference laser light pulses.

In an embodiment of a propellant gas detector system, which may be combined with any previously or subsequently addressed embodiment of a propellant gas detector system, unless in contradiction, the total optical path length for the test laser light pulses is different to the total optical path length for the reference laser light pulses. This enables the test and reference laser light pulses to be received time-shifted with respect to one another and thus be distinguished easily at the one or more than one detectors.

In an embodiment of a propellant gas detector system, which may be combined with any previously or subsequently addressed embodiment of a propellant gas detector system, unless in contradiction, the difference in the total length of the optical pathway for the test laser light pulses and the total length of the optical pathway for the reference laser light pulses is such that the separation of the pulses at the at least one detector is greater than 100 ns. This ensures that the detected test and reference laser light pulses do not overlap and interfere. In practice, 120 ns has been shown to give excellent results.

In an embodiment of a propellant gas detector system, which may be combined with any previously or subsequently addressed embodiment of a propellant gas detector system, unless in contradiction, the optical path for the reference laser light bypasses the sample chamber. This results in a high signal-to-noise ratio and reliable results.

In an embodiment of a propellant gas detector system, which may be combined with any previously or subsequently addressed embodiment of a propellant gas detector system, unless in contradiction, the optical path for the reference laser light pulses is substantially identical to that of the test light laser pulses, i.e. both the reference laser light pulses and the test laser light pulses pass through the sample chamber. This gives a particularly simple and robust construction of optical path architecture.

In an embodiment of a propellant gas detector system, which may be combined with any previously or subsequently addressed embodiment of a propellant gas detector system, unless in contradiction, the laser light generating arrangement comprises a Vertical External Cavity Surface Emitting Laser or a Quantum Cascade Laser. These are two known examples of types of laser capable of operating in the 3.30-3.55 µm wavelength range, the VECSEL being available from Phocone AG and the QCL from Alpes Laser AG.

In an embodiment of a propellant gas detector system, which may be combined with any previously or subsequently addressed embodiment of a propellant gas detector system, unless in contradiction, the propellant gas detector system comprises a pumping arrangement operatively connected with the sample chamber and arranged to draw the sample continuously into and out from the sample chamber at a predetermined substantially constant flowrate. This pump can be of any known types such as a centrifugal pump, an axial flow pump, a Venturi pump (which runs on compressed air or water thus is vibration free). The constant flow rate prevents vibration in the system and oscillation in the gaseous sample, which is particularly advantageous in the case of a multipass sample chamber being used, since these can be sensitive to vibration and gas-stream pulsating in the sample chamber.

In an embodiment of a propellant gas detector system, which may be combined with any previously or subsequently addressed embodiment of a propellant gas detector system, unless in contradiction, the sample chamber and pump are arranged to provide a pressure in the sample chamber of between 10 mbara (millibar absolute pressure) and 1000 mbara, or between 50 mbara and 150 mbara, or substantially 100 mbara. Selecting a particular value in these ranges enables the operator to select a balance between measurement accuracy (higher pressure) and detection speed (lower pressure and thus lower gas transit time through the system). In practice, approximately 100 mbara pressure in the sample chamber gives good results accuracy with a gas transit time of approximately 22 ms using current setups.

The invention is furthermore directed to a container leak testing system comprising a propellant gas detector system according to any of the above embodiments of propellant gas detector systems; and a sampling arrangement operatively connected to the sample chamber of the propellant gas detector system.

In an embodiment of a container leak testing system, which may be combined with any previously or subsequently addressed embodiment of a container leak testing system, unless in contradiction, the sampling arrangement comprises a sniffer in flow connection with the sample chamber of the propellant gas detector system, which may be a sniffer cup, a portal-type arrangement, a pre-chamber placed over the container, or any other conceivable arrangement. This enables simple taking of samples.

In an embodiment of a container leak testing system, which may be combined with any previously or subsequently addressed embodiment of a container leak testing system, unless in contradiction, the container leak testing system comprises a constant-flowrate suction pump operationally connected to the sniffer and to the sample chamber. This enables drawing samples into the sample chamber without causing pneumatic vibrations to which the sample chamber might be sensitive, particularly in the case of a multipass chamber.

In an embodiment of a container leak testing system, which may be combined with any previously or subsequently addressed embodiment of a container leak testing system, unless in contradiction, the suction pump is situated downstream of the sample chamber. This helps to prevent vibrations from the pump e.g. caused by variations in airflow, from being transmitted to the sample chamber, which in the case of a multipass chamber can be sensitive to vibrations.

In an embodiment of a container leak testing system, which may be combined with any previously or subsequently addressed embodiment of a container leak testing system, unless in contradiction, the container leak testing system comprises a container conveyor arrangement arranged to convey a plurality of containers past the sampling arrangement. This enables fast in-line testing at rates of at least 600 tested containers per minute.

In an embodiment of a container leak testing system, which may be combined with any previously or subsequently addressed embodiment of a container leak testing system, unless in contradiction, the sampling arrangement comprises at least two sniffers, and further comprising a container conveying arrangement arranged to convey a plurality of containers alternately past one of the two (or more) snifters. This may enable faster testing rates than possible with a single sniffer. In both embodiments of conveying means, the conveying means may be even linear, curved, or rotary. Advantageously, a crossover valve is arranged to alternately connect each sniffer to the sample chamber, preventing sample dilution and/or cross contamination from the snifter cup not currently taking a sample from around a container.

In an embodiment of a container leak testing system, a constant flow cross-section crossover valve is operationally connected to both snifters and to the sample chamber. This crossover valve connects each sniffer in turn while ensuring a substantially constant flowrate into the sample chamber, which prevents changes in the flowrate from causing vibrations and gas-stream pulsating, which may adversely affect e.g. a multipass sample chamber, and preventing sample dilution and/or cross contamination from the sniffer cup not currently taking a sample from around a container.

In an embodiment of a container leak testing system, which may be combined with any previously or subsequently addressed embodiment of a container leak testing system, unless in contradiction, the sampling arrangement is situated inside an isolation chamber provided with an air curtain generator at the entrance and exit thereof. This isolates the sampling arrangement from the ambient environment, which may be contaminated with propellant.

Furthermore, the air curtain generator purges the ambient air from around the containers and from the surface thereof as they pass into the isolation chamber, further reducing contamination of the testing environment, i.e. the interior of the isolation chamber. This improves the detection accuracy.

In an embodiment of a container leak testing system, the isolation chamber comprises a clean air or clean gas inlet in an upper portion of the isolation chamber. This enables the contents of the isolation chamber to be purged with clean air (i.e. air uncontaminated with propellant, taken e.g. from outdoors) so as to ensure the removal of contamination introduced into the isolation chamber e.g. by a leaking container being present therein. This further improves the detection accuracy.

In an embodiment of a container leak testing system, which may be combined with any previously or subsequently addressed embodiment of a container leak testing system, unless in contradiction, a gas outlet is provided in a lower portion of the isolation chamber, said gas outlet being active, passive, or a combination of active and passive. This further improves detection accuracy by improving the purging of the isolation chamber by providing extraction at the bottom of the chamber.

In an embodiment of a container leak testing system, which may be combined with any previously or subsequently addressed embodiment of a container leak testing system, unless in contradiction, the sampling arrangement comprises at least one pre-chamber placeable around at least part of a container being tested. This pre-chamber can be placed over at least part of a container being tested and thus enables a build-up of leaking propellant in its interior, thus increasing the concentration of leaking propellant sampled compared with merely passing containers past a sniffer. This improves the detection accuracy, and also helps isolate the container being tested from the surrounding environment, which is advantageous in the case when the surrounding environment is contaminated with propellant. It is noted that we understand that the isolation chamber is a static arrangement into which the containers can be brought, whereas the pre-chamber is a mobile structure that can be placed over at least part of a container, and thus moves therewith.

In an embodiment of a container leak testing system, which may be combined with any previously or subsequently addressed embodiment of a container leak testing system, unless in contradiction, the sampling arrangement comprises a purging system in operative connection with the pre-chamber for purging the pre-chamber with clean air or other clean gas. This ensures that any contaminated air or propellant contained within the pre-chamber is flushed and thereby cleaned so that any possible contamination that was in the pre-chamber is removed before the sample is taken, and thus cannot affect the detection accuracy.

In an embodiment of a container leak testing system, which may be combined with any previously or subsequently addressed embodiment of a container leak testing system, unless in contradiction, pre-chamber is in selective or constant operative connection with the sample chamber. This can be carried out either by bringing it directly into connection with the sample chamber, or by passing it underneath or past a sniffer, and thus serves to improve the measurement accuracy by providing the possibility of a greater concentration of leaked propellant gas being entered into the sampling arrangement and thus into the sample chamber, due to the fact that the container stays longer in operative connection with the pre-chamber than it would when simply being passed by a sniffer.

In an embodiment of a container leak testing system, which may be combined with any previously or subsequently addressed embodiment of a container leak testing system, unless in contradiction, the system further comprises coarse leak detection arrangement arranged upstream of the principle propellant gas detection system and a pre-rejection mechanism operatively connected with the coarse leak detection arrangement. This enables the rejection of grossly leaking containers before they reach the more sensitive leak detection mechanism, contaminating the testing environment and possibly resulting in non-leaking containers tested nearby a coarsely-leaking container being inappropriately rejected.

In an embodiment, wherein the coarse leak detection arrangement comprises a flap adjacent to a space for a container and operatively connected with the pre-rejection system. This flap is arranged to be blown by a flow of leaking propellant, and may be arranged to make or break or an electrical contact, or its movement may be detected by optical, electrostatic, or magnetic means. This provides a simple and effective way to detect an extremely leaky container that is "blowing" propellant.

In an embodiment, which may be combined with any previously or subsequently addressed embodiment, unless in contradiction, the container leak testing system further comprising a rejection mechanism operatively connected with the comparing processing unit. This enables containers which have been determined by the processing unit as being leaky to be rejected.

BRIEF DESCRIPTION OF DRAWINGS

The invention will now be described in terms of specific, non-limiting examples in the following figures, which show:

FIG. 11: a graph of the ratio or difference of the test and reference pulses in relation to the example of FIG. 10;

FIG. 12: a schematic plan view of an embodiment of the conveyor and sniffer cup arrangement of FIG. 10;

FIG. 13: a schematic plan view of an alternative embodiment of the conveyor and snifter cup arrangement of FIG. 10;

In the figures, like reference signs denote like components.

DETAILED DESCRIPTION OF EMBODIMENTS

Figure 1:
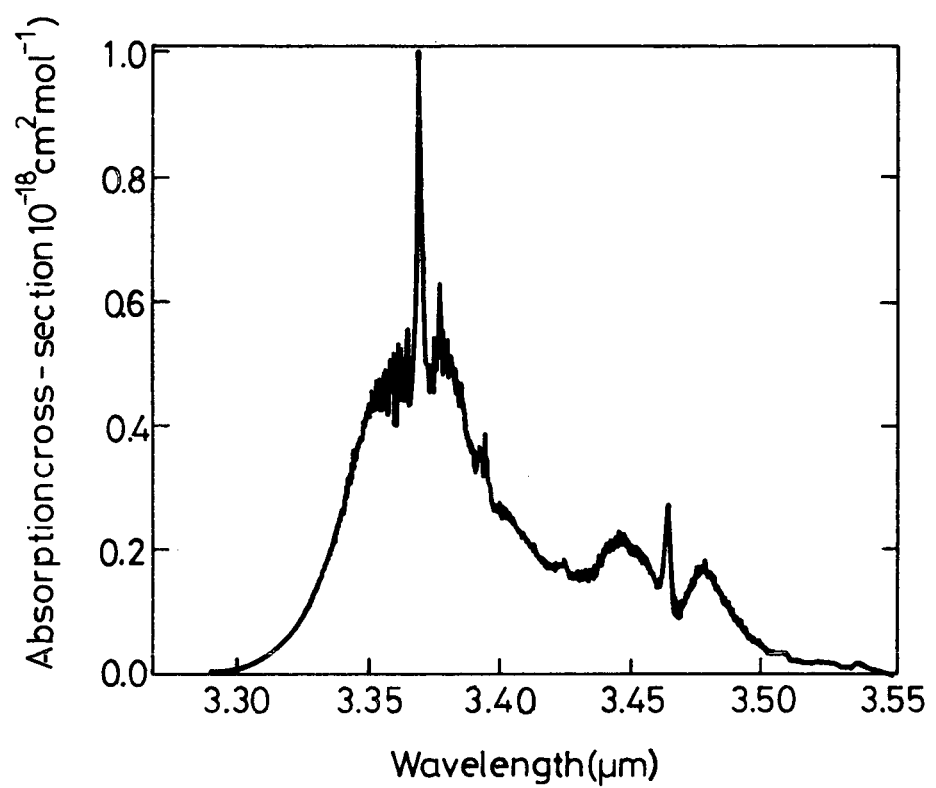
FIG. 1: the absorption spectrum o~ propane and butane exploited by the present invention.

FIG. 1 shows the spectrum range of significant absorption of propane and n-butane in the wavelength range exploited by the present invention. This absorption spectrum range of propane is substantially identical to that of n-butane, hence only one curve is illustrated. I-butane has a similar significant spectrum range, dimethyl ether, methyl ethyl ether, HFA 134a, HFA 227, and other possible propellant gases have differing spectral forms with peaks in the addressed range. To exhibit absorption in the illustrated wavelength range, the propellant gas is believed to have at least one C—H bond in its molecular structure.

Unlike previous optical methods operating in the 7.2 µm wavelength range, the addressed absorption spectrum range of FIG. 1 does not overlap with that of water or other atmospheric components, hence detection of the presence of the above-mentioned propellants does not require complex spectral analysis to distinguish. This absorption spectrum range is substantially located between 3.30-3.55 µm wavelength. Laser light with a spectrum situated anywhere in or including this wavelength range, when passed through a sample containing at least one of the addressed propellants, or any other propellant exhibiting absorption in the requisite wavelength range, will be at least partially and significantly absorbed by said propellant, and will thus be attenuated. When this laser light is compared with substantially equal laser light which did not pass through the sample, it there is generically a difference in amplitude between pulsed laser light which did go through the sample and pulsed laser light which did not go through the sample, and which cannot be accounted for by e.g. differences in path length e.g. in air, dust etc., then the presence of propellant is confirmed. It is noted that, unlike prior art methods, the present method does not rely on spectral analysis: the pulse amplitudes independent of frequency composition of the pulsed laser light are compared, which is a substantial simplification over the prior art.

Figure 2:
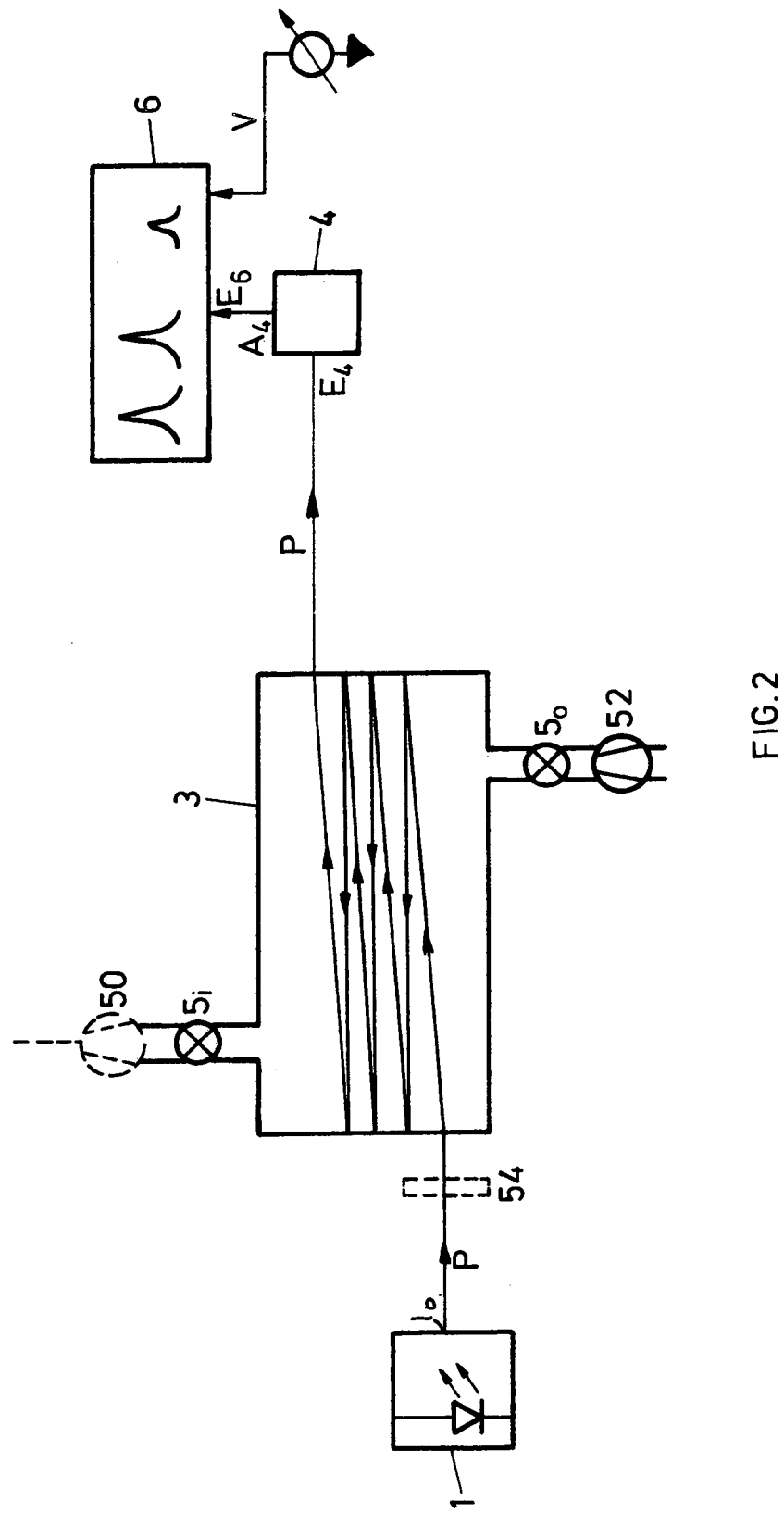
FIG. 2: a schematic illustration of a first embodiment of the invention operating according to the method according to the invention.

FIG. 2 shows schematically a basic embodiment of a system according to the present invention and operating a method of the invention exploits the absorption spectral range of FIG. 1. Laser light source 1 generates a series of pulses of laser light the spectrum thereof being at least partially situated in the wavelength range of 3.30-3.35 lim. These pulses travel on path P. which may be at least partially constituted by fibre optics, through a sample chamber 3, towards and onto a detector 4. Sample chamber 3 is a multipass chamber, that is to say the laser light passes through the chamber multiple times between entrance and exit by means of mirrors, thus exposing the laser light to as much propellant as necessary. Alternatively, a single pass cell of sufficient length can be used, which applies equally to the below-mentioned embodiments. The size of the multipass chamber 3 is a compromise between sufficiently rapid gas exchange time, which is greater for a cell of lower volume, and the amount of absorption, which is greater for a longer path length of laser light through the multipass chamber 3. However, longer path lengths require larger chambers and/or more reflections, leading to increased complexity and cost of the sample chamber. In practice, it has been shown that a 300 cm3 multipass sample chamber with a 36 m path length works well, however the volume and path length may be chosen as desired.

When there is known to be no propellant in sample chamber 3, the laser light pulses are considered to be reference pulses, and are received at detector 4 at an amplitude of e.g. $A_{ref}$. If it is not known whether there is propellant present in the sample chamber 3, the laser light pulses are considered to be test laser light pulses. When a detectable concentration of propellant is introduced into sample chamber 3, e.g. via one or more of optional input and/or output valves $5_o$, $5_i$ a portion of the laser light pulses is absorbed by the propellant, resulting in a measurable reduction of amplitude of the pulses received at input $E_4$ of detector 4. This reduction of amplitude is detected by signal processor 6, to which output $A_4$ of detector 4 is operationally connected.

Figure 3:
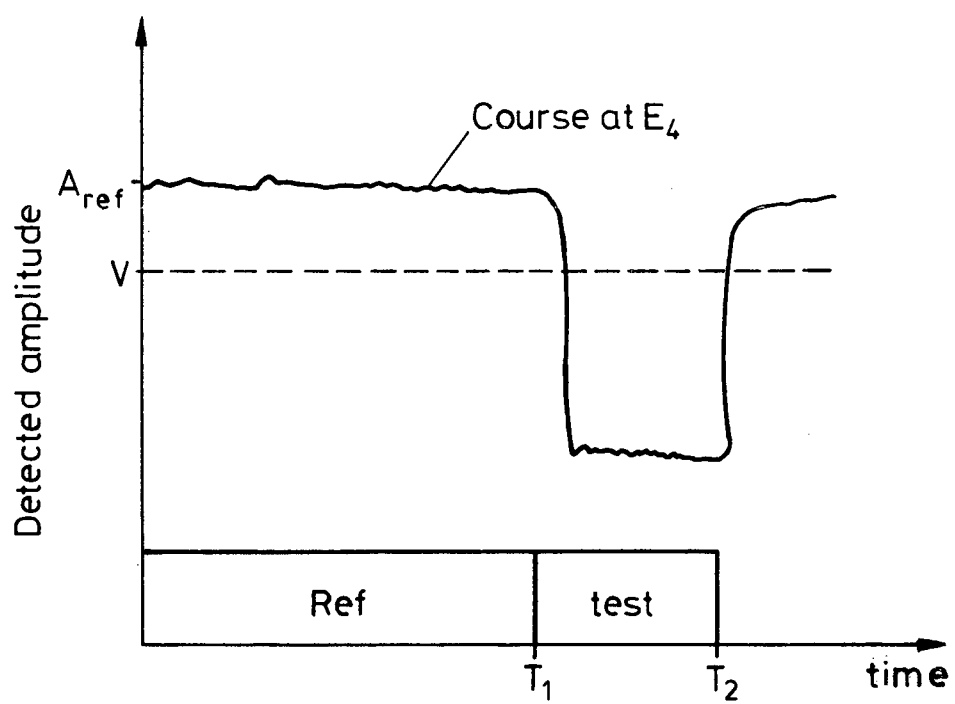
FIG. 3: a qualitative graph of the received pulse amplitude versus time related to the first embodiment as of FIG. 2.

FIG. 3 illustrates the detection principle by qualitative time-course: laser light source 1 produces at output $1_o$ laser light pulses at a predefined repetition rate. When there is no propellant in the sample chamber 3, the amplitude of the detected laser light signals is ideally constant $A_{ref}$ and the laser light pulses "Ref" are considered to be reference laser light pulses. When it is not known whether propane and butane is present in sample chamber 3, the laser light pulses are considered to be test laser light pulses "Test". At time $T_1$, a sample containing a quantity of propellant is introduced into the sample chamber 3, causing the amplitude of the detected signals, i.e. that of the test laser light pulses during "Test", to drop below selectable threshold value V. Signal processor 6 detects this reduction in amplitude below threshold value V, and thereby indicates the presence of propellant in sample chamber 3. At time $T_2$, the sample is exhausted from sample chamber 3, causing the amplitude of the detected signals to return to $A_{ref}$. Automatic adjustment of the threshold value V may be carried out according to a statistical evaluation analogue to that disclosed in EPO 791814.

Returning to FIG. 2, this embodiment can either be operated as a batch process, introducing and exhausting individual samples via valves $5_i$; $5_o$ or can be operated continuously by flowing samples in a carrier gas such as in air, nitrogen, argon, or similar. This equally applies to the other embodiments of FIGS. 4, 5, 7, 8, and 9. Thereby a stream of carrier gas with the samples should be as continuous as possible so as to avoid artifacts which might be introduced by a pulsating stream.

To improve the detection accuracy, the sample concentration in the sample chamber 3 can be increased by increasing the pressure in the sample chamber 3, for instance by means of increasing the pressure with an upstream pump as shown at 50 in dash line in FIG. 2 and conceiving e.g. valve $5_o$ as a pressure regulating valve. Nevertheless, in one embodiment a downstream pump 52 is provided, keeping stable pressure in the sample chamber 3 on a vacuum level. Pressurising chamber 3 causes more light to be absorbed by increased partial pressure of propellant which may be present in sample chamber 3. Additionally or alternatively, the length of path P through the sample chamber 3 can be increased, e.g. by using a longer sample chamber and/or a sample chamber with more multipass reflections. Thereby extended exposure of the laser light pulses to any propellant contained within sample chamber 3 is achieved, resulting in increased absorption and thereby improved measurement accuracy. Both of these principles—pressuring chamber 3, lengthening optical path in chamber 3—can equally be applied individually or in combination to any other of the embodiments described below.

Downstream the laser light source 1 an optical filter 54 may be provided for tailoring the spectrum of laser light as exploited. This likewise equally applies to all the embodiments disclosed below. Furthermore, in the embodiment of FIG. 2, constituting at least part, or even all, of the laser light path P situated out of the sample chamber 3 (i.e. the path from the laser light source 1 to the sample chamber 3, and the path from the sample chamber 3 to the detector 4) from optical fibre would result in a very robust structure.

Figure 4:
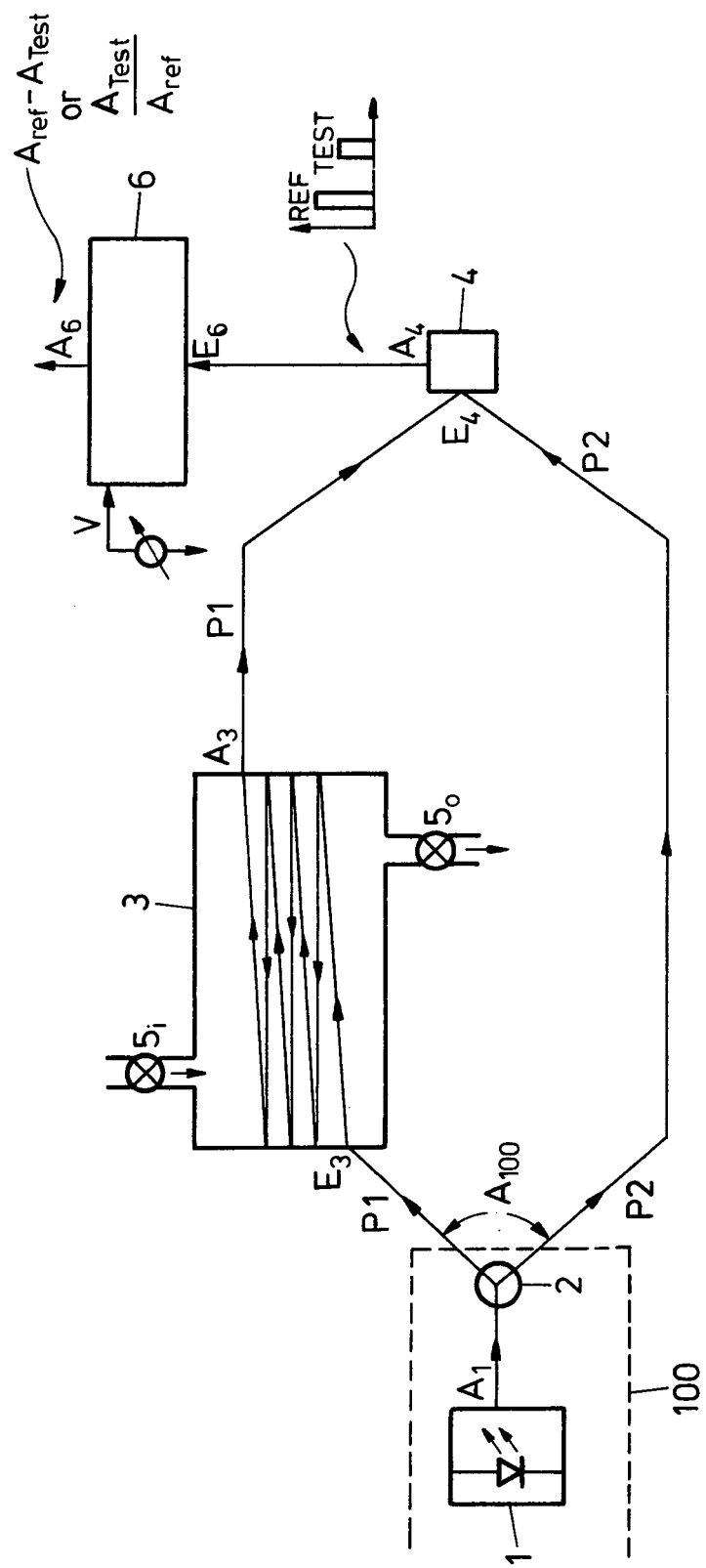
FIG. 4: a schematic illustration of a second embodiment of the invention.

FIG. 4 shows schematically an embodiment as practiced today.

Laser light source 1 generates at its output AI a series of laser light pulses, the spectrum of the laser light being at least partially situated in the wavelength range of 3.30-3.55 μm. In a practiced embodiment, it has a spectrum limited to 3.30-3.35 μm. The laser source 1 can be based on a VECSEL (Vertical Cavity Surface Emitting Laser) or a QCL (Quantum Cascade Laser) laser source, examples of which operating in the desired wavelength range having recently become available from the firms Phocone AG and Alpes Laser AG respectively.

The pulsed laser light is split by a beam splitter 2 into test laser light pulses travelling on test optical path P1, and reference light pulses travelling on reference optical path P2. Thus, source 1 and beam splitter 2 in fact constitute a source arrangement 100 with an output $A_{100}$ for test-laser light pulses and reference laser light pulses. Test path P1 passes through multipass sample chamber 3, with the laser light pulses passing through the sample chamber 3 volume a number of times between entering $E_3$ and exiting $A_3$ the chamber 3. After exiting sample chamber 3 at $A_3$, test path P1 leads to input $E_4$ of detector 4. Reference path P2 bypasses the sample chamber 3, and travels directly to input $E_4$ of detector 4.

A gaseous sample can be received in sample chamber 3. e.g. via optional valves $5_i$, $5_o$. In today's realisation, the gaseous sample is received in a continuous stream of carrier gas, e.g. air. In fact, a good mode of operation is such continuous stream of carrier gas (e.g. air, nitrogen) with samples carried within it and sufficiently separated such that mixing between samples cannot occur up to and including sample chamber 3.

In a good embodiment the portions of test path P1 situated outside chamber 3 are optically identical to the reference path P2, i.e. the optical path outside of the sample chamber 3 is substantially identical (as far as is practical) for both test path P1 and reference path P2. If the addressed paths P1 and P2 are established in air, this means that the length of test path P1 in ambient air is the same as the length of path P2 in ambient air and has the same optical treatment along these. This ensures that any attenuation, noise, dust and other optical impacts are experienced to the same degree both by the test laser pulses and the reference laser pulses.

In the present example, due to the total path length of test path P1 being longer than that of reference path P2, the time of arrival of the test laser light pulses and of the reference laser light pulses is staggered in time. In this example, this is achieved by the path length of test path P1 through multipass sample chamber 3. For instance, in the case of a 10 ns pulse repeated at a repetition rate of 10 kHz (i.e. one pulse every 100 μs), the difference in the length of path P1 to path P2 can be tailored so as to separate the arrival o~ the reference laser light pulse and of the test laser light pulse by about 120 ns, by providing a path length through sample chamber 3 of 36 m. Other and thereby shorter time-separations of the pulses are possible so long as the two pulses can be distinguished from each other by their arrival time at input $E_4$ clearly. Clearly, e.g. in the case of a single pass sample chamber 3, the total path length of reference path P2 may be chosen to be longer than that of path P1, thereby achieving the same effect but with the opposite order of arrival of the pulses. Nevertheless by doing so the path P2 may lose its role for reference to some extent because, optically, it is more difficult to tailor the longer path P2 optically as identical as possible to the shorter path P1 outside sample chamber 3. Thus the overall effects of the multipass sample chamber 3 is twofold, namely to stagger the arrival of the test and reference pulses at the detector 4, and to increase absorption compared with a single-pass chamber.

The output $A_4$ of detector 4 is operationally connected to input $E_6$ of signal processing unit 6, where the amplitudes of the detected reference signal pulse and the amplitude of the detector test signal pulse are compared and output at $A_6$. If the difference in amplitude as of $A_{ref} - A_{Test}$, or the ratio in amplitude as of $A_{Test}/A_{ref}$ of these pulses "REF" and "TEST" is above (or below depending on the selected ratio or the difference calculated) a threshold value V, then the presence of propellant in the test cell is confirmed. If the laser light source 1 emits pulses at a rate of 10 kHz, 10,000 measurements per second are achieved, leading to an excellent signal-to-noise ratio, since a large number of measurements may be averaged over the time span a gas sample travels through the sample chamber 3. Any other measurement rate is of course possible as desired. It should also be noted that, as above, at least part of one or more of the laser light paths may be constituted by optical fibre. This point applies equally to all the other embodiments described below. If required, statistical evaluation analogue to that disclosed in EP0791814 for the threshold value can be applied: This applies equally to all embodiments.

Figure 5:
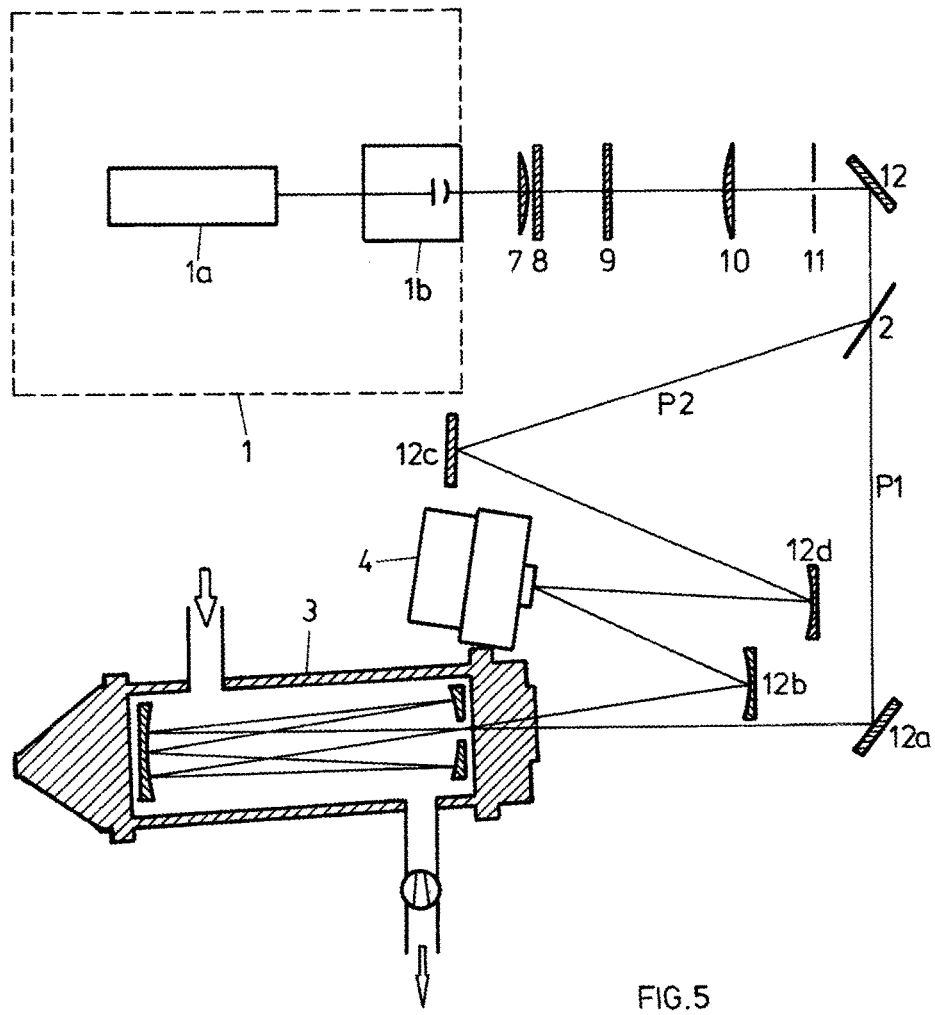
FIG. 5: a more detailed schematic illustration of the laser pulse paths of the embodiment of FIG. 4.

FIG. 5 illustrates in greater detail the embodiment of FIG. 4. Laser light source 1 comprises an EDFA (Erbium-Doped Fibre Amplifier) pump laser 1a pumping, in this specific case, a 3.3 μm VECSEL laser 1b. It is self-evident, however, that other types of pump laser can be used, and that a QCL or any other suitable laser, pumped or not, operating in the desired wavelength range can be substituted for VECSEL laser 1b. In this case, the output of the laser light source 1 passes through a lens 7, polarizer 8, a filter 9, a further lens 10 and a collimator 11. Beam splitter 2, which may be any type of beam splitter with equal absorption for both splitted parts of the laser beam, such as a semi-silvered mirror divides the laser light along a test path P1 for the test laser light pulses, and along a reference path P2 for the reference laser light pulses. Path P1 leads via mirror 12a through a 300 cm³ multipass cell constituting the sample chamber 3.

The length of path P1 through this specific multipass cell is 36 meters. After exiting the sample chamber 3, path P1 leads via mirror 12b to detector 4. Path P2 leads from beam splitter 2 via mirror 12c and a mirror 12d to detector 4 bypassing multipass cell 3. The path P1 from splitter 2 to input of chamber 3 and from output of chamber 3 to detector 4 is optically as identical as possible to the path P2 from splitter 2 to detector 4. Nevertheless, the exact geometry and path lengths illustrated in FIG. 5 are not to be construed as limiting: alternate geometries are possible according to the exact component layout of the system. As above, portions of the laser pathways may be constituted by optic fibres.

Figure 6:
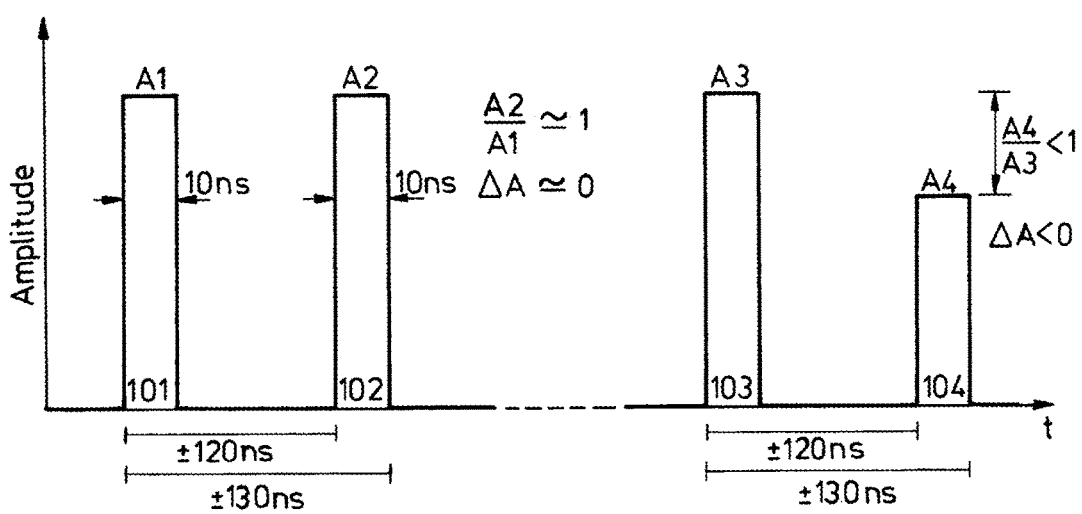
FIG. 6: a graph of received signal amplitudes versus time related to the second embodiment.

FIG. 6 shows one variation of the principle of the ratio or difference of the amplitude as used in the detection systems illustrated in FIGS. 4 and 5. Reference pulse 101 and test pulse 102 illustrate qualitatively a situation when no propellant is present in the sample chamber 3, i.e. no leaking container is being detected, and reference pulse 103 and test pulse 104 illustrate qualitatively a situation when propellant from a leaking container is present in sample chamber 3. Each of the pulses is approximately 10 ns in duration, and test pulses 102, 104 arrive approximately 120 ns after the corresponding reference pulses. It is self-evident that other pulse durations and other pulse separations are possible as required. The first pair of pulses 101, 102, have substantially the same amplitude, i.e. amplitude $A1 \simeq A2$, and therefore the ratio of the pulse amplitudes $A2/A1 \simeq 1$, and the difference between the pulse amplitudes $A2-A1 \simeq 0$.

In the case of the pair of pulses 103, 104, due to absorption of part of the laser light of test pulse 104 by propellant in sample chamber 3, amplitude A4 of pulse 104 is less than the amplitude A3 of pulse 103, i.e. A4<A3. In consequence, the ratio of the pulse amplitudes A4/A3<1, and the difference between the pulse amplitudes A4–A3<0. If the ratio or difference (as is being used at the time) is less a threshold value, then the presence of propellant in the sample chamber 3 is confirmed.

It is self-evident that the ratios or differences may be calculated in the opposite fashion so as to give opposite results, i.e. leading to the ratio or difference rising above a threshold value on detection of propellant. The skilled person understands how to calculate this and how to arrange the signal processing unit to do so and to determine in consequence the presence or absence of propellant in the sample chamber 3. Further, a multitude of pulse pairs 101/102 and 103/104, or the difference or the ratio thereof may be averaged, and this average used for determination of the presence or absence of propellant in the sample chamber 3.

Figure 7:
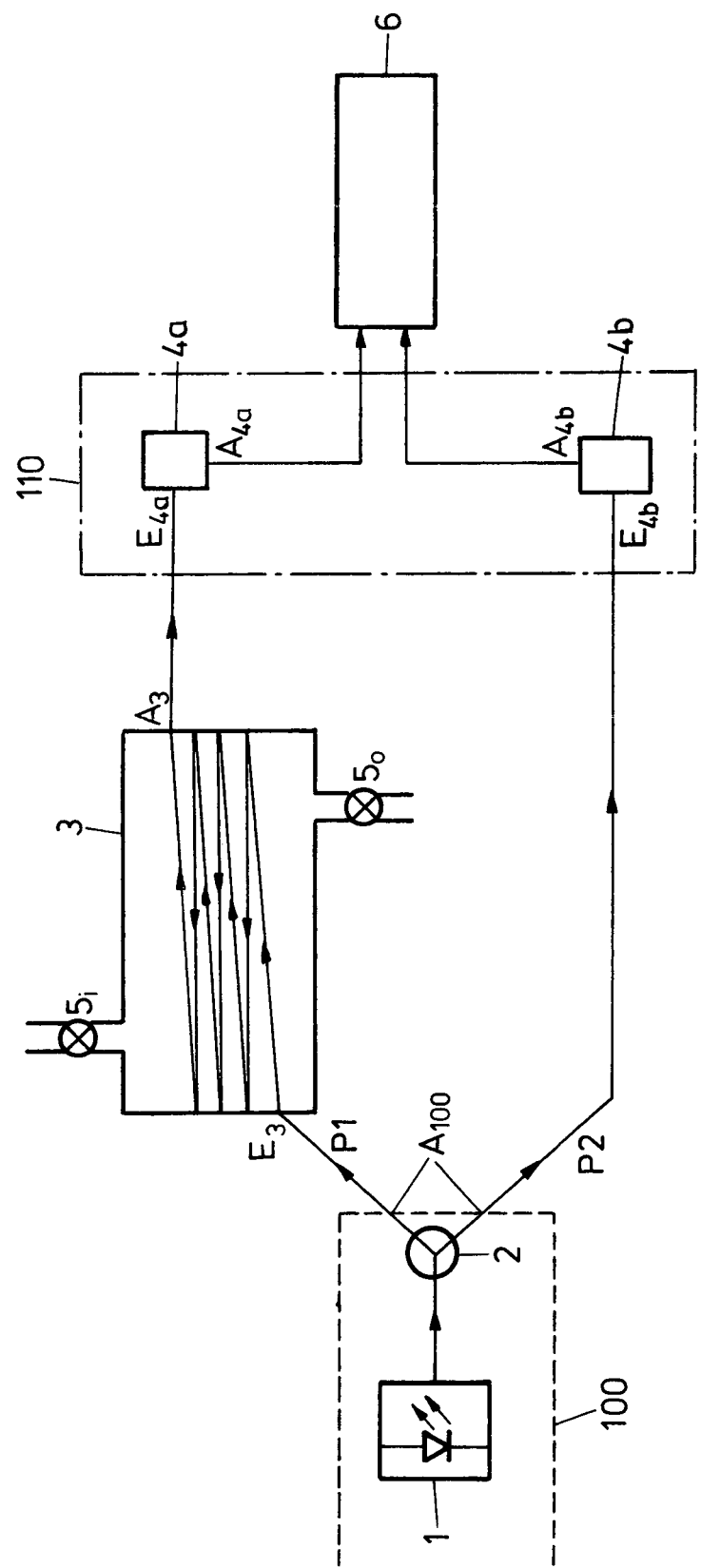
FIG. 7: a schematic illustration of a third embodiment of the invention.

FIG. 7 illustrates a third embodiment of the system and method according to the invention which differs from that of FIG. 4 in that, instead of a single detector 4, a pair of detectors 4a and 4b with inputs for laser light $E_{4a}$ and $E4_b$ respectively, together forming a detector arrangement 110 are used for detecting the test laser light pulses and the reference laser light pulses respectively. Signals output by detector outputs $A_{4a}$ and $A_{4b}$ respectively are input to signal processing unit 6 at its inputs. Since detectors 4a and 4b may not be identical, calibration may be required. This variant does not require staggering the test pulses and reference pulses in time, since the test laser light pulses and the reference laser light pulses are received by respective detectors and can then be compared even if they arrive coincidentally. It is, however, equally applicable to non-coincident arrival of the test and reference pulses e.g. by storing the amplitude of the pulse first for further evaluation as may be done in the embodiments of FIGS. 4 and 5.

Figure 8:
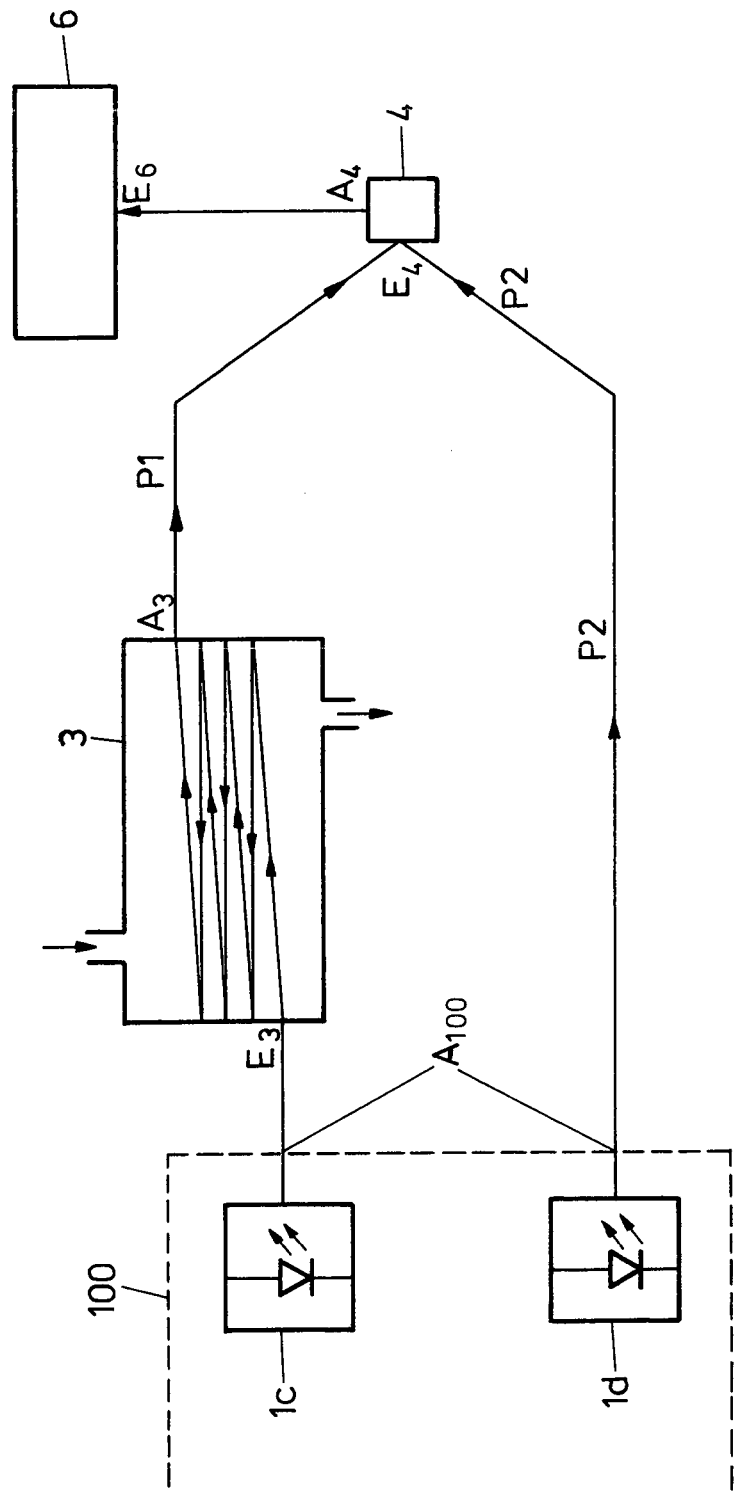
FIG. 8: a schematic illustration of a fourth embodiment of the invention.

FIG. 8 shows a fourth embodiment differing from that of FIG. 4 in that the test laser light pulses are generated by a first laser source 1c, and reference laser light pulses are generated by a second laser source 1d forming laser source arrangement 100. As in FIG. 4, a single detector 4 is used, path P1 is longer than path P2 so as to stagger the arrival of the test laser light pulses and of the reference laser light pulses at input E4 of the detector 4. Calibration and/or synchronisation of the two laser light sources may be required.

Figure 9:
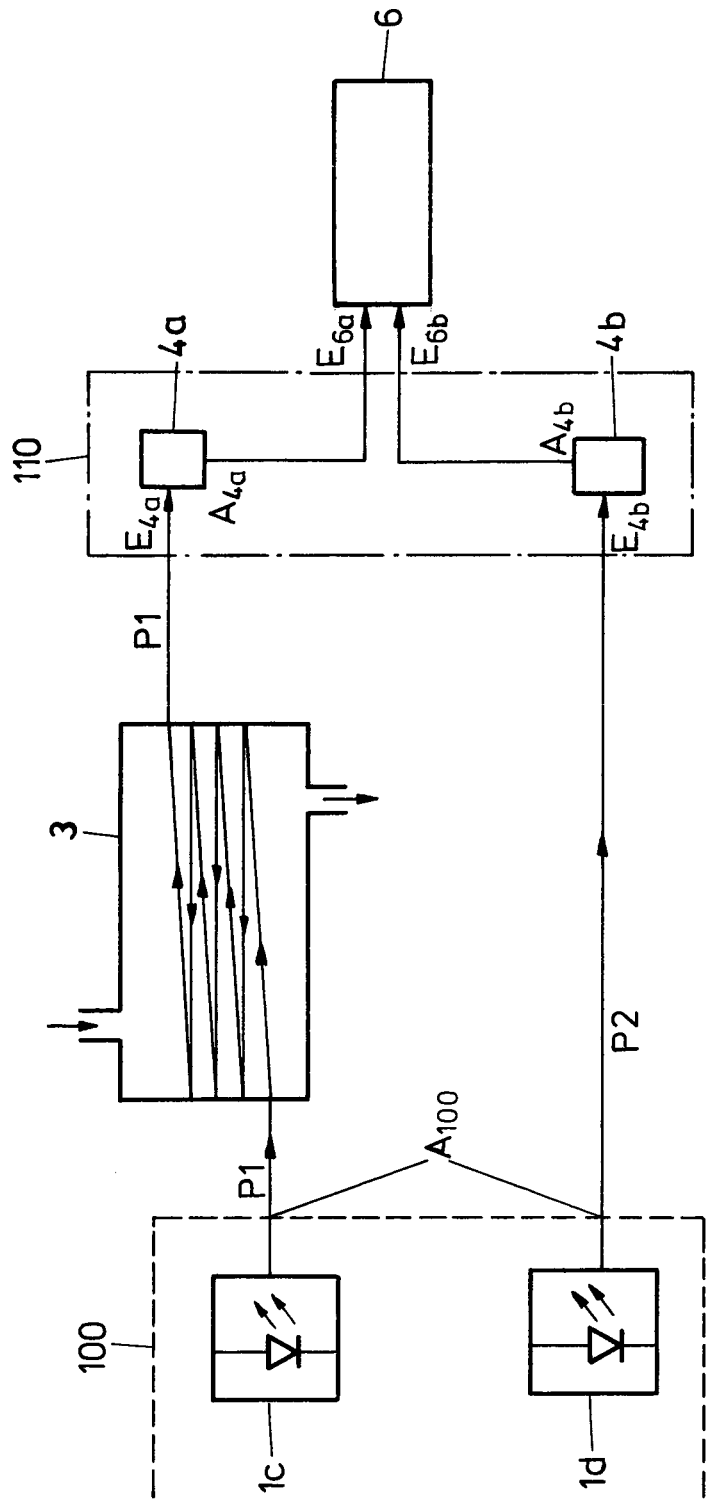
FIG. 9: a schematic illustration of a fifth embodiment of the invention

FIG. 9 represents a fifth embodiment combining the embodiment of FIG. 7 and the embodiment of FIG. 8, in that two separate laser light sources 1c, 1d form laser light source arrangement 100, and two detectors 4a and 4b with inputs for laser light $E_{4a}$ and $E_{4b}$ respectively (cf. FIG. 7), form a detector arrangement 110. Path P1 leads from laser light source 1c, through sample chamber 3, to detector 4a. Path P2 likewise leads from laser light source 1d to detector 4b, bypassing sample chamber 3. As above, calibration and/or synchronisation of the laser light sources and calibration of the detectors may be required.

Figure 10:
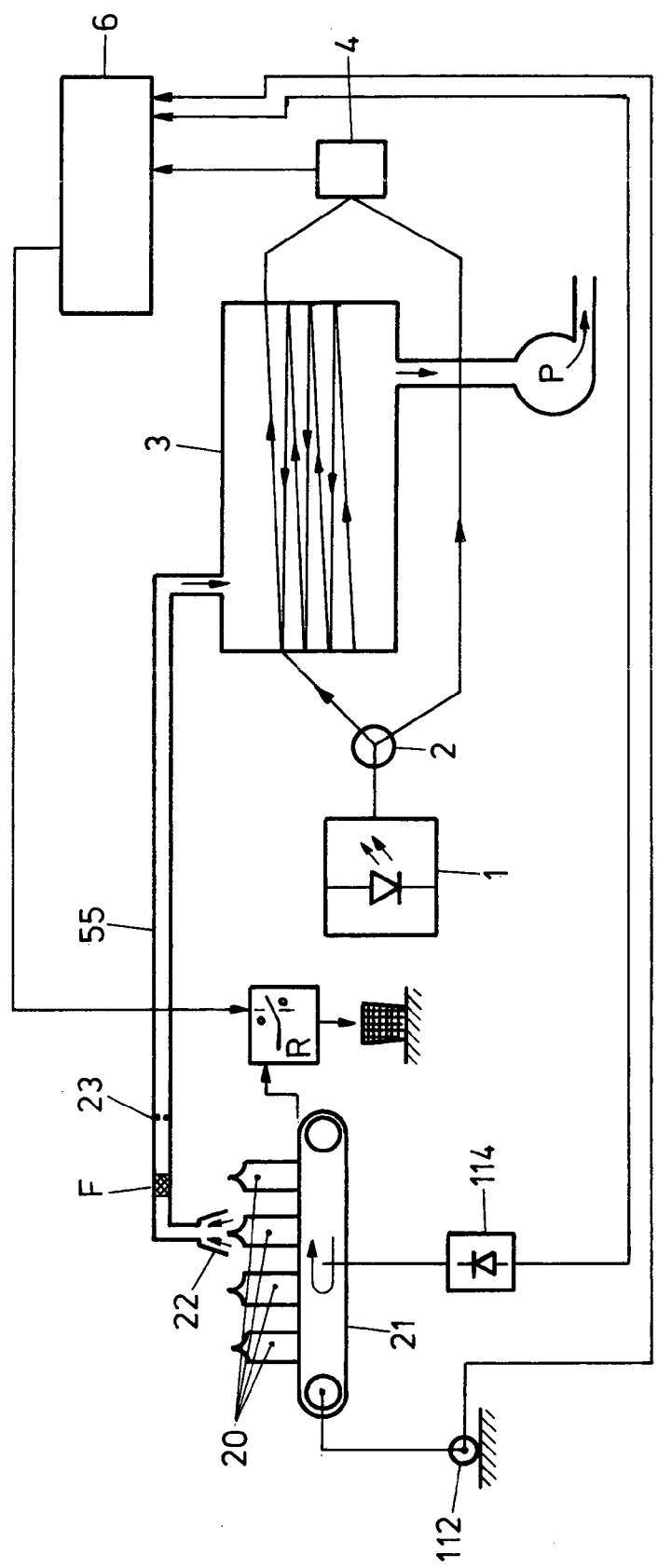
FIG. 10: a serial container leak testing system incorporating the second embodiment of the invention.

FIG. 10 shows a system for leak testing containers 20 containing propellant. These could be e.g. aerosol cans containing propellant as a propellant, or fuel canisters, e.g. for camping gas stoves, which use propane and/or butane as the product and as a propellant. A conveyor system 21 of any known type (i.e. linear, curved, or rotary) sequentially presents containers 20 to a sniffer arrangement 22 at a constant rate. Pump P, which may be of any known continuously operating type, creates a partial vacuum in the sample system, thereby drawing samples taken from around the respective containers 20 situated proximate to the sniffer arrangement cup 22, via optional filter F optional pressure stage 23, along conduit 55 and through the sample chamber 3 of a detection system according to the embodiment of FIG. 4 or 5 as described above. Since in this embodiment the samples are drawn in continuously at a substantially constant flow rate, optional valves 5 illustrated in FIG. 2 are not provided or are left open. The system is arranged such that pressure in the sample chamber 3 is between 10 mbara (milibar absolute) and 1000 mbara, the exact pressure being chosen as a compromise between the gas stream flow rate and the ability to detect approximately 100 ppm of propellant, e.g. propane and/or butane in the sample: higher pressure leads to increased measurement accuracy due to a higher partial pressure of propellant being present in the chamber, whereas lower pressure leads to a shorter gas transit time and thereby to an increased testing throughput rate. As an alternative, a high-pressure variant could be possible with the pump situated between the sniffer arrangement 22 and the gas inlet to the sample chamber 3, the outlet of the sample chamber 3 being provided with a pressure-regulating flow restrictor to maintain a desired pressure in the sample chamber 3.

If the signal processor 6 detects the presence o~ propellant in the sample chamber 3 above a predetermined threshold value corresponding to an unacceptable leakage rate from the container 20, an automatic rejection mechanism R is operated to reject the containers in question from the production line. In practice, detection of a specific leaking container is deferred by approximately 22 ms at a system pressure of approximately 10 mbara, which is primarily due to the sample transit time from the sniffer arrangement 22 to the sample chamber 3.

Thus, and as the specific container at a conveyer-rate of 600/mm (50 ms) this container is still present at the sniffer arrangement 22, 22 ms deferred from its arrival at the arrangement 22.

The detection system does not need to be "synchronised" with the conveyor system for the automatic rejection mechanism R to reject the leaking container, since the detection and comparing result relate to the container still in the sniffer-position. However, if the time lag between arrival of a container 20 into the sniffer-position and presence of the test result becomes too long or if conveyance speed varies, then such time lag I and/or speed $V_c$ needs to be taken into account to properly assign test results to the correct containers. Also, if the rejection mechanism is situated downstream of the sniffer-position, as shown in FIG. 10, this would also have to be taken into account to synchronise the rejection mechanism with the containers to be rejected: the skilled artisan knows how to perform this.

The additional system parameters of conveyer speed detected e.g. at conveyer drive 112, and arrival of a container in sniffer-position as detected by a sensor 114 may be fed to the processing unit 6 to properly assign the result to the corresponding container to be rejected.

Although FIG. 10 shows the detection system of the embodiment of FIG. 4 or 5, any of the other illustrated variants could be used in its place. In the case of the embodiment of FIG. 2 being used, the reference laser light pulses are generated when there are no containers present in the system, or by presenting a previously-leak-tested container to the sniffer arrangement 22, or by calibrating based on the gap between individual containers 20. A sudden reduction in amplitude of the received pulses would then indicate the presence of a leaking container and thereby cause automatic rejection mechanism R to be operated. As a further variation, multiple detection systems can be incorporated with a switchover system to direct the gaseous samples to each detection system in turn. Alternatively, a single detection system with multiple sample chambers 3 can be used with a similar switchover system for directing the gaseous samples, and with a single laser source directing the laser light pulses alternately through each sample chamber by means of an optical switch, e.g. a piezoelectrically operated mirror.

The detection principle of the embodiment of FIG. 10 when integrated into such a leak testing arrangement is qualitatively illustrated in FIG. 11. This figure shows a qualitative graph of the output of the comparing operation, i.e. the output of processing unit 6 in time units of 0.1 seconds. At a throughput rate of 600 per minute, this results one container being tested every 0.1 seconds.

The signal s is the ratio or the difference between the amplitude of a received test laser light pulse and the amplitude of a received reference laser light pulses preferably just ahead or just following the test laser light pulse.

X is the ratio or the difference between the amplitude of the test and that of reference pulses when no propane and butane is present in the sample chamber 3. If not considering the path through sample chamber 3, the optical path P1 is the same as the optical path P2, X will then be substantially 1 for the ratio, or zero for the difference. When propellant from a leaking container is present in the sample chamber 3, part of the test laser light pulses will be absorbed thereby. Thus the amplitude of the received test laser light pulses will be decreased, causing the ratio between the amplitude of the test and reference laser light pulses to be reduced, or causing the difference between the amplitude of the test and reference laser light pulses to become negative, causing signal s to drop.

Figure 14:
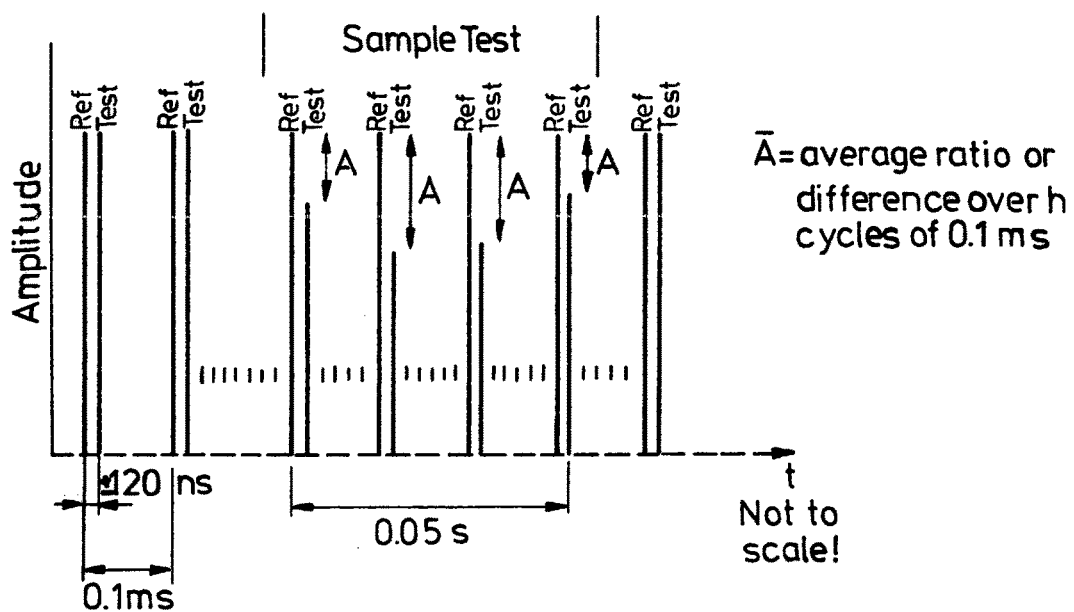
FIG. 14: a qualitative time course of a sample of gas being sampled.

At a testing rate of 600 containers per minute, 10 containers are tested per second, i.e. one container every 0.1 second. Since the laser emits 10 ns pulses at a repetition rate of 10 kHz, every 0.1 s contains 1000 individual measurements. If a container is present within range of the sniffer for 50% of this time, then 500 individual measurements per container are carried out which can be low pass filtered or averaged over a time period so as to improve the signal accuracy. It should be noted that the addressed amplitudes may accord with the averaging result according to A of FIG. 14, which shows a number of representative reference and test pulse pairs as a leaking container passes below a sniffer.

The ratio or difference A calculated as in FIG. 6 for a number n of pulse pairs may be averaged to determine whether the container is leaking or not.

In the graph of FIG. 11, we can see that the containers being tested at 0.3 s and 1.0 s from the arbitrary start time Os are leaking, and the signal processing unit will therefore command automatic rejection mechanism R to reject these containers.

Self-evidently, if the ratio or differences were to be calculated in the opposite manner, detection of propellant will cause the ratio or difference to rise, in which case signal s would be inverted with respect to how it is illustrated in FIG. 11.

FIG. 12 illustrates plan view of a simple conveyor system 21 for the leak testing system of FIG. 10 combined with a single sniffer cup arrangement 22. Containers 20 are conveyed by conveyor system 21 in a single line. Automatic rejection mechanism R is situated so as to be able to remove leaking containers from the line based on a command from the signal processing unit 6. Automatic rejection mechanism R may be of any known type. Although a linear conveyor system has been illustrated here, a rotary system is also possible.

FIG. 13 illustrates an alternate conveyor system in which two staggered lines of containers 20 are presented alternately to a pair of sniffer cups 22a, 22b. The sniffer cups 22a, 22b may be simply connected in parallel with each other to sample chamber 3, or may be connected alternately with sample chamber 3 by means of crossover valve 23. The crossover valve 23 maintains a constant flow cross section.

The operation of valve 23 is synchronous with the feed of the containers 20. This arrangement potentially permits an increased throughput of containers. As with FIG. 12, the conveyor system can be rotary instead of linear, or may comprise a pair of rotary conveyors presenting containers 20 alternately to a pair of sniffers 22a, 22b of the overall sniffer-arrangement.

In many container filling and testing environments, contamination of the ambient air with propellant gas can be a problem. Normal mitigation strategies including floor-level extraction limit this to a certain degree: the propellant gases in question are denser than air and thus tend in any case to sink downwards. However, these mitigation strategies may not be sufficient to prevent ambient propellant gas from affecting the readings of the propellant leak-detection system. A simple solution to this problem is to situate the sampling arrangement as far off the ground as possible, ideally at least 1.2 meters off the ground.

Figure 15:
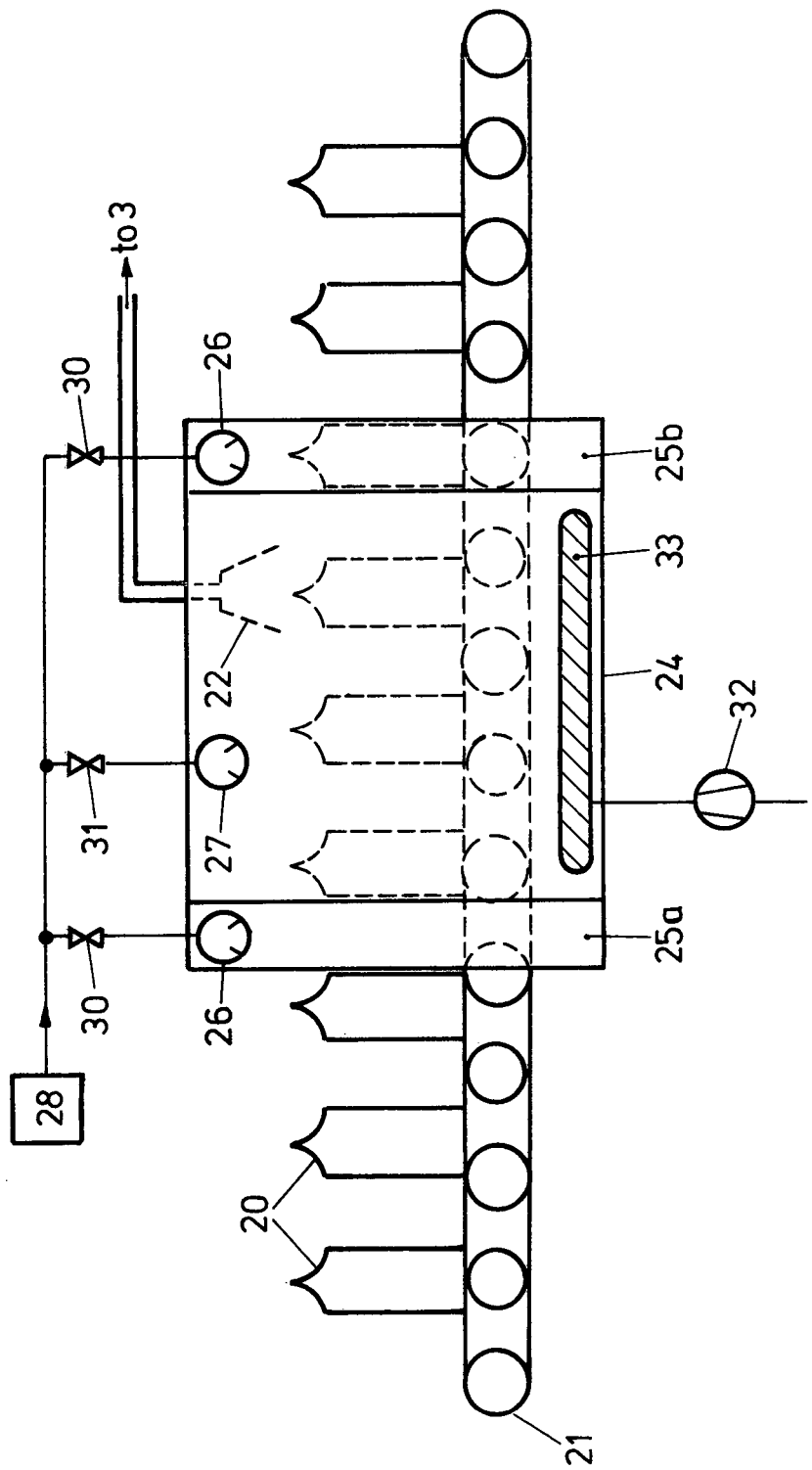
FIG. 15: a schematic representation of a testing arrangement incorporating an isolation chamber.

FIG. 15 illustrates schematically a further solution to this problem, referred to as "conditioning". As in FIGS. 10, 12, and 13, conveyor 21 (which may be linear, rotary, or any other type) conveys containers 20 past a sniffer 22, which draws in samples and passes them to sample chamber 3 (not illustrated in FIG. 14). Sniffer 22, which may be of any type as above, is situated in an isolation chamber 24 provided with an air curtain 25a, 25b, at each end, through which the containers 20 pass. Compressed gas supply 28 supplies compressed the fresh air (e.g. from gas bottles, or drawn in from the outside air and thus uncontaminated with propellant) via optional valves 30 to outlets 26 which create the aircurtains. Alternatively, nitrogen, argon, or another inert gas could be used in place of air. Additionally, fresh air or other uncontaminated gas for purging the isolation chamber 24 may be introduced into the isolation chamber 24 above the containers 20 (i.e. from the top) via inlet 27, and gas from inside the isolation chamber 24 may be extracted from the bottom of the isolation chamber 24 via outlet 33, drawn by pump 32. Although the illustrated gas streams are shown as coming from a common gas supply 28, this does not need to be the case: the air curtains for instance may be supplied by one gas supply, whereas the gas introduced into the isolation chamber 24 may come from a different supply or indeed be omitted altogether. Likewise, outlet 33 may be omitted if not required, for instance if the air curtains 25a, 25b create enough air motion to cause the air inside isolation chamber 24 to be constantly replenished, and to leave e.g. via openings (not illustrated) in the bottom of isolation chamber 24. Furthermore, the air curtain 25a at the entrance to the isolation chamber 24 helps to serve to purge contaminants from the surroundings of the containers 20.

Accordingly, the interior of isolation chamber 24 is isolated from the ambient air by the air curtains 25a, 25b, and any contamination introduced into the isolation chamber 24 e.g. by a leaking container 20 is quickly drawn away via outlet 33.

A rejection mechanism (not shown) of any convenient type may be arranged as convenient, either inside isolation chamber 24 or thereafter.

Figure 16:
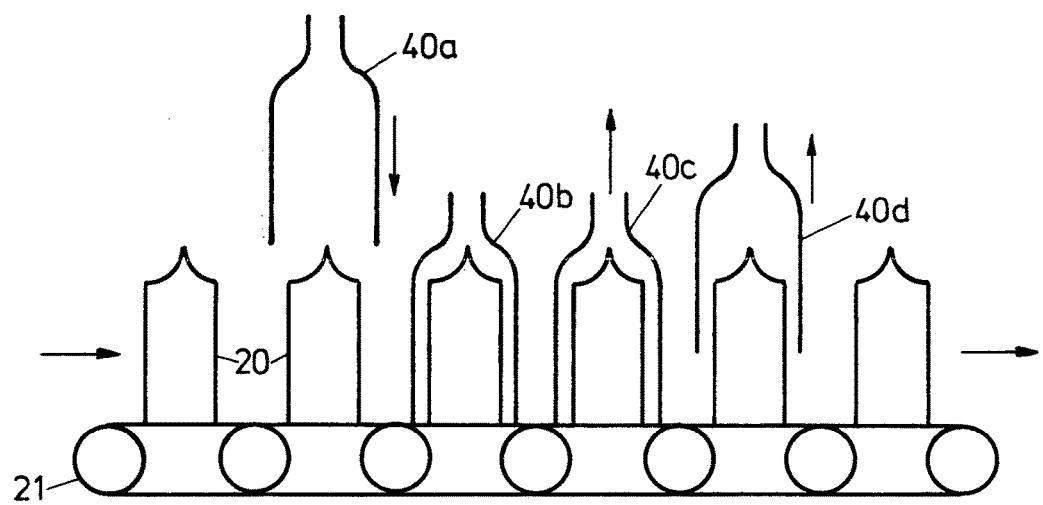
FIG. 16: a schematic representation of a testing arrangement incorporating pre-chambers.

FIG. 16 illustrates schematically an alternative embodiment incorporating conditioning. A number of pre-chambers 40a-40d arranged above a conveyor 21 (which may be linear, rotary, or any other type) upon which containers 20 are conveyed sequentially. The pre-chambers are fed on a heeding arrangement synchronously with containers 20 on conveyor 21. The arrangement of conveyor 21 and pre-chambers 40 may be analogous to that of current carousel-type vacuum-based leak-detection systems as produced by the applicant. Pre-chamber 40 is lowered over a container 20, as illustrated as 40a, and is purged with clean air or other gas e.g. nitrogen introduced from the top. This purging may take place while pre-chamber 40a is being lowered, and/or after it has been lowered and has reached its lowest position, and serves to purge any propellant or contaminated ambient air from the pre-chamber and the sides of the container 20. Next, as illustrated with pre-chamber 40b, the pre-chamber 40 is left around container 24 a certain time, so as to allow a concentration of propellant to build up inside pre-chamber 40 in the case that the container is leaking: this further increases the measurement accuracy since a greater concentration of leaking propellant will be sniffed compared with merely passing containers beneath a sniffer. Next, as illustrated with pre-chamber 40c, a sample is extracted from the pre-chamber and passed to the test chamber 3 of a propellant leak detection system as described above, either by "sniffing" the pre-chamber in a manner analogue to the direct sniffing of the containers illustrated in FIG. 10 above, or by connecting it directly to the test chamber 3. If desired, a suction pump (not illustrated) may be provided to further speed the extraction of the sample from the pre-chamber. Finally, as illustrated as 40d, the pre-chamber 40 is removed from around the container 20. As above, a rejection mechanism according to any known type (not illustrated) is arranged as convenient for rejecting leaking containers.

Generically, all of the above-mentioned "conditioning", contamination-reducing, systems can be described as first purging contaminants from around the containers with clean air or other clean gas, then collecting the gaseous sample for testing.

Figure 17:
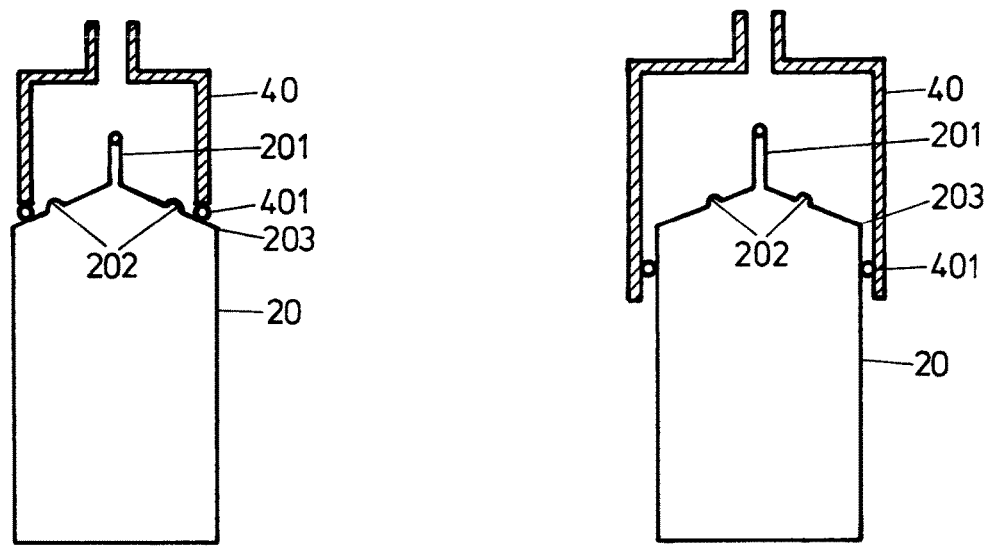
FIG. 17: a schematic representation of pre-chambers only covering part of a container.

The pre-chambers 40 may be full-size, i.e. covering the whole of the container 20, and may or may not comprise a seal between pre-chambers 40 and the conveyor 21. Alternatively, the pre-chambers 40 may be of partial length, covering a part of the container 20, e.g. to just past the shoulder 203, or containers covering just the valve 201 and crimp 202 on the container 20, both illustrated in FIG. 17. Optional seal 401 may seal the pre-chamber 40 to the container 20. The seals 401 may be pneumatically operated.

Figure 18:
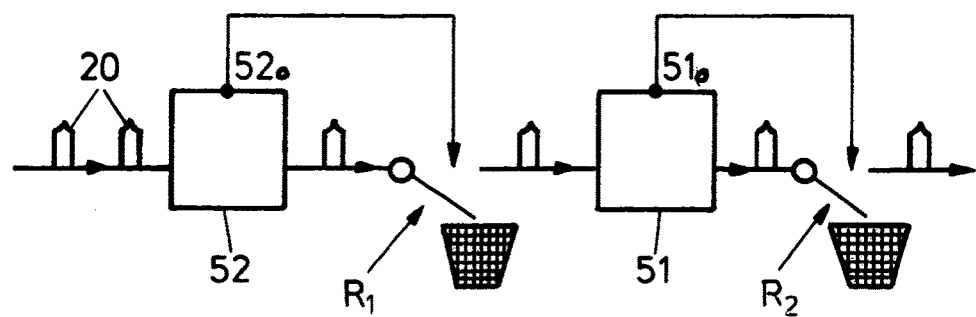
FIG. 18: a schematic representation of a two-stage coarse-fine propellant leak detection system.
Figure 19:
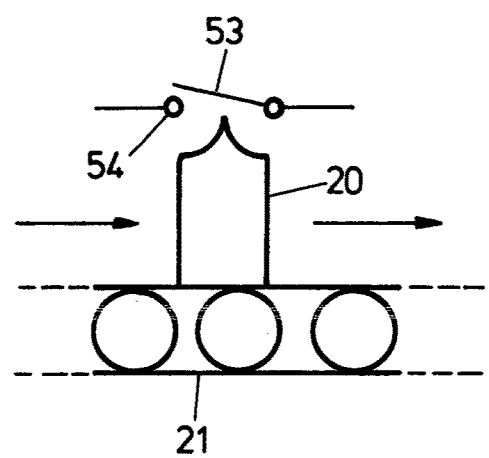
FIG. 19: a schematic representation of a coarse leak detection system.

A further way to reduce contamination of the testing environment with propellant is illustrated schematically in FIG. 18. It can be the case that a container is leaking so heavily that significant quantities of propellant are "blowing" from the valve and/or the crimp. If such a container were to enter the testing environment, i.e. in proximity to the sniffer 22 or pre-chamber 40, or into isolation chamber 24, the large amounts of propellant being emitted can compromise the measurements and possibly lead to rejection of non-leaky containers due to this cross contamination. This is resolved with a two-stage testing process. Upstream of propellant leak detection system 51, which may be of any of the above-disclosed types, and its rejection mechanism $R_2$ controlled by output $51_o$ of propellant leak detection system 51, is a coarse propellant leak detection system 52, which controls a pre-rejection system R1 via its output $52_o$. As illustrated in FIG. 19, coarse propellant leak detection system 52 may incorporate a lightweight flap-type detection system under which containers 20 are conveyed, and arranged such that a coarse propellant leak of a certain flow rate (i.e. a "blowing" container) will cause a flap 53 to be blown upwards by the escaping gas and thereby break an electrical contact 54, the flap 53 constituting the armature of an electrical switch. Alternatively, movement of the flap may make a contact in the opposite manner to the above, or the flap may actuate a micro-switch to make or break an electrical contact. Other alternatives are optical, electrostatic, or magnetic detection of movement of the flap 53 in response to escaping gas. Alternatively, a local overpressure detection may be used, or an optical method utilising the principle of refraction of light caused by escaping gas.

If coarse propellant leak detection system 52 detects heavy leaking of a container 20, a signal is output at 520 which controls pre-rejection system R1 so as to reject the container in question and prevent it from entering the propellant leak detection system 51, and thus prevent contamination of the testing environment of propellant leak detection system 51. Coarse propellant leak detection system 52 may be situated as convenient in a production line between the filling o~ the containers and propellant leak detection system 51

Figure 20:
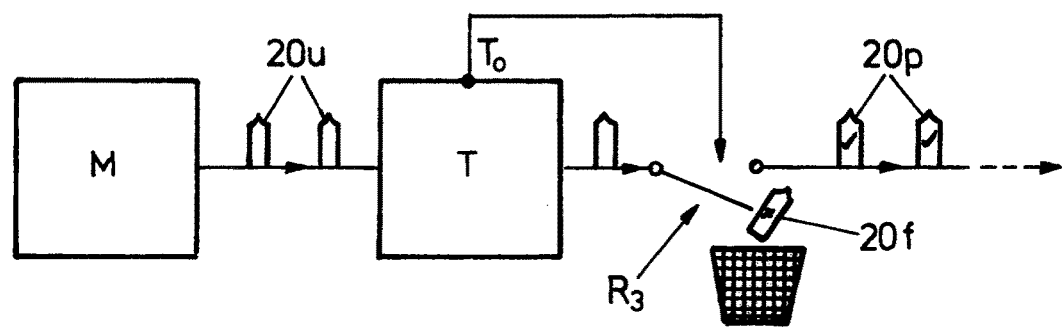
FIG. 20: a schematic, generic representation to a system for manufacturing unleaky containers.

FIG. 20 shows schematically and generically a system for manufacturing unleaky containers. In block M, containers are manufactured and filled, producing untested containers $20u$. These untested containers $20u$ are then passed to block T, where they are tested by any of the above-described methods in any of the above-described propellant leak detection systems. Leaky containers $20f$ are rejected by rejection mechanism $R_3$ based on output of the propellant leak detection system output at $T_o$. In the case of a course-fine double detection system as illustrated in FIG. 18, rejection mechanism $R_3$ naturally incorporates both rejection mechanisms $R_1$ and $R_2$ from that figure.

Rejection mechanism $R_3$ may also be incorporated into block T. Unleaky containers $20p$, having passed the leak detection test are thus considered manufactured and are then passed on for further processing such as capping, application of labels, boxing, shipping to customers and so on.

While a full attempt has been made to describe the invention by means of various specific embodiments, these are not to be construed as limiting the scope of the invention, which is defined solely by the scope of the appended claims. In particular, it is noted that all embodiments may be combined as long as the result is not contradictory.

Finally, clauses relating to how the invention is generically practiced today are given in the following:

Clause A. Method of leak-testing containers containing at least one propellant gas selected from the group of propane, n-butane, i-butane, dimethyl ether, methyl ethyl ether, HFA 134a, HFA 227, comprising the steps of:
  obtaining a gaseous sample taken from the surroundings of a container;
  receiving the gaseous sample in a sample chamber;
  generating test laser light pulses and reference laser light pulses, the spectrum of the light pulses being each situated at least partially within a spectral range of 3.30-3.55 µm wavelength;
  passing the test laser light pulses through the sample chamber, and passing the reference laser light bypassing the sample chamber;
  detecting the test laser light pulses and the reference laser light pulses;
  comparing the amplitude of at least one detected test laser light pulse with the amplitude of at least one detected reference laser light pulse so as to determine the presence or absence of said propellant above a predetermined threshold concentration in the sample chamber.

Clause B. Method according to the preceding clause, wherein the test laser light pulses are passed through the sample chamber multiple times.

Clause C. Method according to any preceding clause, wherein the test laser light pulses and the reference laser light pulses are generated by beam splitting laser light pulses generated by a single laser light source.

Clause D. Method according to any proceeding clause, wherein the test laser light pulses and the reference laser light pulses are detected by the same detector, and the total optical path length travelled by the test laser light pulses is different to that travelled by the reference laser light pulses such that the test and reference laser light pulses do not mutually interfere at the detector.

Clause E. Method according to any preceding clause, wherein the gaseous sample is drawn into the sample chamber in a continuous manner, for instance by a suction pump.

Clause F. Method according to any proceeding clause, wherein a plurality of containers are sequentially conveyed past at least one snifter, a sample being taken from the surroundings of each container as it passes the sniffer.

Clause G. Method according to the preceding clause, wherein the plurality of containers are sequentially conveyed alternately past at least two sniffers, valve means being optionally provided to bring each individual snifter into communication with the sample chamber in turn and synchronously with the passing of the containers.

Clause H. Method of manufacturing unleaky containers containing at least one propellant gas selected from the group of propane, n-butane, i-butane, dimethyl ether, methyl ethyl ether, HFA 134a, HFA 227, comprising the steps of:
  manufacturing filled, untested containers;
  leak-testing said containers according to the leak-testing method of any proceeding clause;
  if said propellant gas is detected in the sample chamber as being above the predefined threshold concentration, rejecting said container under test;
  if said propellant gas is detected in the sample chamber below the predefined threshold concentration, accepting said container under test as an unleaky container.

Clause I. Container leak-testing system to leak-test containers containing at least one propellant gas selected from the group of propane, n-butane, i-butane, dimethyl ether, methyl ethyl ether, HFA 134a, HFA 227, comprising:
- a sample chamber;
- a sniffing arrangement in fluid communication with the sample chamber;
- a laser light generating arrangement with an output for test laser light pulses and for reference laser light pulses, said laser light pulses having a spectrum situated at least partially within a spectral range of substantially 3.30-3.55 µm wavelength;
- a detector arrangement with a detector input for test laser light pulses and reference laser light pulses and with a detector output, said output of said laser light generating arrangement for test laser light pulses being operationally connected to said detector input via said sample chamber, and said output of said laser light generating arrangement for reference laser light pulses being operationally connected to said detector input bypassing said sample chamber;
- a comparing processing unit with a processing input and processing output;
- said detector output being operationally connected to said processing input;
- said comparing processing unit generating and said processing output a result signal of a comparison of the amplitude of the said test laser light pulses and the amplitude of the said reference laser light pulses.

Clause J. Container leak-testing system according to the preceding clause, wherein the sample chamber is a multipass sample chamber.

Clause K. Container leak-testing system according to clause I or J, wherein the laser light generating arrangement comprises a single laser source, and wherein a beam splitter is arranged to split laser light pulses from the single laser source into said test laser light pulses and said reference laser light pulses.

Clause L. System according to any of clauses I-K, wherein the detection means comprise a single detector for the laser light pulses, and the total path length for the test laser light pulses is different to that for the reference laser light pulses such that the test and reference laser light pulses do not mutually interfere at the detector.

Clause M. System according to any of Clauses I-L, wherein pumping means, e.g. a suction pump, are arranged so as to draw the gaseous sample into the sample chamber in a continuous manner.

Clause N. System according to any of Clauses I-M, further comprising conveying means arranged to convey a plurality of containers sequentially past at least one sniffer and arranged so as to permit a sample to be taken from the surroundings of each container as it passes the sniffer.

Clause 0. System according to the preceding clause, wherein the conveying means are arranged to convey a plurality of containers sequentially and alternately past at least two snifters, valve means arranged to bring each individual snifter into communication with the sample chamber in turn and synchronously with the passing of the containers being optionally provided.

Clause P. System for manufacturing leak-tested containers containing at least one propellant gas selected from the group of propane, n-butane, i-butane, dimethyl ether, methyl ethyl ether, HFA 134a, HFA 227, comprising:
- manufacturing means for manufacturing untested containers;
- filling means for filling the containers at least partially with said at least one propellant gas;
- a system for leak-testing the containers according to any of clauses I-P;
- rejection means for rejecting containers which are determined to be leaking.

Furthermore, the various conditioning systems can be generically described as in the following clauses:

Q. Method of obtaining a gaseous sample from the surroundings of a container, comprising the steps of:
- purging the surroundings of the chamber with clean air or other clean gas; subsequently
- obtaining a gaseous sample from the surroundings of the container.

R. Method according to clause Q wherein the purging takes place by passing the container through an air curtain defining an entrance to an isolation chamber, and wherein the obtaining of the gaseous sample takes place inside said isolation chamber.

S. Method according to clause R wherein further purging is carried out inside the isolation chamber by means of introducing clean air or other clean gas into an upper portion of the isolation chamber and extracting, either actively or passively, air or gas from a lower portion of the isolation chamber.

T. Method according to clause Q wherein a pre-chamber is lowered over the container, said pre-chamber being purged with clean air or other clean gas while the pre-chamber is being lowered over the container and/or once the pre-chamber has been lowered over the container, and wherein the gaseous sample is obtained from the interior of the pre-chamber.

U. System for obtaining a gaseous sample from the surroundings of a container, comprising:
- a purging arrangement;
- a sampling arrangement situated downstream of the purging arrangement.

V. System according to clause U wherein the purging arrangement is an air curtain arrangement defining an entrance to an isolation chamber, and wherein the sampling arrangement is situated inside said isolation chamber.

W. System according to clause V, wherein a further purging arrangement is arranged inside the isolation chamber in an upper portion thereof, and an active and/or passive extraction arrangement is arranged in a lower portion of the isolation chamber.

X. System according to clause U comprising a pre-chamber operatively connectable with a container or with the surroundings thereof and forming at least part of the sampling arrangement, said pre-chamber being operatively connectable with a source of clean air or other clean gas so as to further constitute at least part of the purging arrangement.

The invention claimed is:

1. A method of detecting the presence of at least one propellant gas in a gaseous sample, comprising the steps of:
- receiving the sample in a sample chamber;
- generating test laser light pulses and reference laser light pulses, the spectrum of at least the test laser light pulses being at least partially within a wavelength range of 3.30-3.55 µm wherein absorption is indicative for the presence of the at least one propellant gas;
- passing at least the test laser light pulses through the sample chamber;
- detecting the test laser light pulses and the reference laser light pulses with at least one detector;
- comparing the amplitude of at least one detected test laser light pulse with the amplitude of at least one detected reference laser pulse so as to determine the presence or absence of the at least one propellant gas above a predetermined threshold concentration in the sample chamber, wherein the at least one propellant gas exhibits absorption in a wavelength range of a laser used for generating said test laser light pulses, wherein the at least one propellant gas is at least one selected from the group consisting of propane, n-butane, i-butane, dimethyl ether, methyl ethyl ether, 1,2,1,2-tetrafluoroethane and 1,1,1,2,3,3,3-heptafluoropropane, wherein the test laser light pulses and the reference laser light pulses are generated by beam splitting pulsed laser light from a single laser source, wherein the test laser light pulses and the reference laser light pulses are detected by the same, single detector, wherein the test laser light pulses and the reference laser light pulses are simultaneously generated by the single laser source, wherein the total length of an optical path travelled by the test laser light pulses is different from the total length of an optical path travelled by the reference laser light pulses, and wherein the length of an optical path in ambient air travelled by the test laser light pulses is substantially equal to the length of an optical path in ambient air travelled by the reference laser light pulses.

2. The method according to claim 1, wherein the sample chamber is a multipass chamber and the test laser light pulses travel through the sample chamber in a plurality of passes.

3. The method according to claim 1, wherein the difference in length of the optical path travelled by the test laser light pulses and the reference laser light pulses is such that there is a separation in time of the pulses at the at least one detector of greater than 100 ns.

4. The method according to claim 1, wherein said reference laser light pulses bypass the sample chamber.

5. The method according to claim 1, wherein the reference laser light pulses are generated when there is known to be substantially no propellant in the sample chamber and said reference laser light pulses are passed through the sample chamber.

6. The method according to claim 1, wherein the laser light pulses are generated by a laser selected from the group consisting of a vertical-cavity surface-emitting laser and a quantum cascade laser.

7. The method according to claim 1, wherein the laser light pulses are generated at a repetition rate of 5-15 kHz.

8. The method according to claim 1, wherein the laser light pulse duration is between 5-15 ns.

9. The method according to claim 1, including flowing the sample continuously through the sample chamber by drawing the sample in by a pump operating at a predetermined substantially constant flowrate.

10. The method according to claim 9, wherein the sample chamber and pump are arranged so as to provide a pressure of between 10 mbara and 1000 mbara in the sample chamber.

11. A method of leak-testing containers containing at least one propellant gas comprising the steps of:
obtaining a gaseous sample taken from the surroundings of a container;
testing said sample according to the method of detecting of claim 1.

12. The method according to claim 11, wherein the gaseous sample is taken from the surroundings of the container by means of a sniffer.

13. The method according to claim 12, including drawing in the gaseous sample to the sniffer at a substantially constant flowrate by means of a suction pump.

14. The method according to claim 13, wherein said suction pump is situated downstream of the sample chamber.

15. The method according to claim 12, wherein a plurality of containers to be leak tested are inline-conveyed sequentially in stream past the sniffer.

16. The method according to claim 12, wherein a plurality of containers to be leak tested are conveyed sequentially and alternately past at least two sniffers.

17. The method according to claim 16, wherein each sniffer is brought into fluid connection with the sample chamber in turn as a container is conveyed past one of the at least two sniffers.

18. The method according to claim 17, wherein each sniffer is brought into fluid connection with the sample chamber in turn as a container is conveyed past the respective sniffer by means of a crossover valve of constant flow cross-section.

19. The method according to claim 11, including purging the surroundings of the container from which the gaseous sample is to be taken with clean air or other clean gas before the sample is taken.

20. The method according to claim 19, wherein the surroundings of the container are purged by passing the container through at least one air curtain.

21. The method according to claim 20, wherein said air curtain defines an entrance to an isolation chamber, a further air curtain being provided and defining the exit of said isolation chamber, the gaseous sample being obtained from the surroundings of the container when said container is within said isolation chamber.

22. The method according to claim 21, wherein the clean air or other clean gas is introduced into an upper portion of said isolation chamber so as to generate a top-to-bottom flow of air or gas in said isolation chamber.

23. The method according to claim 21, including extracting the air or other gas in the isolation chamber from a lower portion of said isolation chamber.

24. The method according to claim 11, including taking the gaseous sample from the surroundings of the container by means of a pre-chamber.

25. The method according to claim 24, including purging the pre-chamber with clean air or other clean gas before taking the sample.

26. The method according to claim 24, including passing the pre-chamber past a sniffer in said taking the gaseous sample.

27. The method according to claim 24, wherein the sample is taken by bringing the interior of the pre-chamber into flow connection with the sample chamber.

28. A method of manufacturing unleaky containers containing at least one propellant gas, comprising the steps of:
manufacturing filled, untested containers;
leak-testing said containers according to the leak testing method of claim 11;
if said at least one propellant gas is detected in the sample chamber as being above the predefined threshold concentration, rejecting the container from the surroundings of which the gaseous sample was taken;
if said at least one propellant gas is detected in the sample chamber below the predefined threshold concentration, accepting the container from the surroundings of which the gaseous sample was taken as an unleaky container.

29. A method of manufacturing unleaky containers containing at least one propellant gas, comprising the steps of:

manufacturing filled, untested containers;
subjecting the containers to a further leak detection test, a container failing this further leak detection test being rejected;
leak-testing non-rejected containers according to the leak testing method of claim 11;
if said at least one propellant gas is detected in the sample chamber as being above the predefined threshold concentration, rejecting the container from the surroundings of which the gaseous sample was taken;
if said at least one propellant gas is detected in the sample chamber below the predefined threshold concentration, accepting the container from the surroundings of which the gaseous sample was taken as an unleaky container.

30. The method according to claim 29, wherein said further leak detection test comprises passing the container beneath a flap arranged to react to a predetermined threshold gas flow rate, detecting this reaction, and actuating a rejection mechanism based on this detection.

31. A propellant gas detector system comprising:
a sample chamber;
a laser light generating arrangement with an output for reference laser light pulses and for test laser light pulses, said laser light having a spectrum at least partially within a wavelength range of 3.30-3.55 µm wherein absorption is indicative for the presence of said propellant gas, said propellant gas exhibiting absorption in a wavelength range of a laser of the laser light generating arrangement used for generating said test laser light pulses;
a detector arrangement with a detector input for test laser light pulses and reference laser light pulses and with a detector output, said output of said laser light generating arrangement being operationally connected to said detector input via said sample chamber; and
a comparing processing unit with a processing input and a processing output,
wherein the detector output is operationally connected to said processing input,
wherein the comparing processing unit generates at said processing output a result signal of a comparison of the amplitude of the said test laser light pulses and the amplitude of the said reference laser light pulses,
wherein the laser light generating arrangement comprises a single laser source, and wherein a beam splitter is provided in operational connection with the single laser source and upstream of the input to the sample chamber,
wherein the detector arrangement comprises a single detector,
wherein the test laser light pulses and the reference laser light pulses are simultaneously generated by the single laser source,
wherein a total optical path length for the test laser light pulses is different from a total optical path length for the reference laser light pulses, and
wherein an optical path in ambient air for the test laser light pulses is substantially the same length as an optical path in ambient air for the reference laser light pulses.

32. The propellant gas detector system according to claim 31, wherein the sample chamber is a multipass chamber.

33. The propellant gas detector system according to claim 31, wherein the difference in length of the optical path for the test laser light pulses and the optical path for the reference laser light pulses is such that there is a separation in time of the pulses at the at least one detector of greater than 100 ns.

34. The propellant gas detector system according to claim 31, wherein an optical path for the reference laser light pulses bypasses the sample chamber.

35. The propellant gas detector system according to claim 31, wherein the laser light generating arrangement comprises a laser selected from the group consisting of a vertical-cavity surface-emitting laser and a quantum cascade laser.

36. The propellant gas detector system according to claim 31, wherein the sample chamber and pump are arranged to provide a pressure in the sample chamber of between 10 mbara and 1000 mbara.

37. A container leak testing system comprising:
a propellant gas detector system according to claim 31;
a sampling arrangement operatively connected to the sample chamber of said propellant gas detector system.

38. The container leak testing system according to claim 37, wherein the sampling arrangement comprises a sniffer in flow connection with the sample chamber.

39. The container leak testing system according to claim 38, further comprising a constant-flowrate suction pump operationally connected with the sniffer and with the sample chamber.

40. The container leak testing system according to claim 39, wherein said suction pump is situated downstream of the sample chamber.

41. The container leak testing system according to claim 37, further comprising a container conveyor arrangement arranged to convey a plurality of containers past the sampling arrangement.

42. The container leak testing system according to claim 37, wherein the sampling arrangement comprises at least two sniffers, and further comprising a container conveying arrangement arranged to convey a plurality of containers alternately past each sniffer.

43. The container leak testing system according to claim 42, wherein a constant flow cross-section crossover valve is operationally connected to each sniffer and to the sample chamber.

44. The container leak testing system according to claim 37, wherein the sampling arrangement is situated inside an isolation chamber provided with an air curtain generator at the entrance and exit thereof.

45. The container leak testing system according to claim 44, wherein the isolation chamber comprises a clean air or clean gas inlet in an upper portion of the isolation chamber.

46. The container leak testing system according to claim 44, wherein a gas outlet is provided in a lower portion of the isolation chamber.

47. The container leak testing system according to claim 37, wherein the sampling arrangement comprises at least one pre-chamber placeable around at least part of a container being tested.

48. The container leak testing system according to claim 47, wherein the sampling arrangement comprises a purging system in operative connection with the pre-chamber for purging the pre-chamber with clean air or other clean gas.

49. The container leak testing system according to claim 47, wherein the at least one pre-chamber is in selective or constant operative connection with the sample chamber.

50. The container leak testing system according to claim 37, further comprising a further leak detection arrangement arranged upstream of the propellant gas detector system and a pre-rejection mechanism operatively connected with the further leak detection arrangement.

51. The container leak testing system according to claim 50, wherein the further leak detection arrangement comprises a flap adjacent to a space for a container and operatively connected with the pre-rejection mechanism.

52. The container leak testing system according to claim 37, further comprising a rejection mechanism operatively connected with the comparing processing unit.

53. The method according to claim 1, wherein said propellant gas has at least one C—H bond in its molecular structure.

54. The propellant gas detection system according to claim 31, wherein such propellant gas has at least one C—H bond in its molecular structure.

55. The propellant gas detector system according to claim 31, further comprising a pumping arrangement operatively connected with the sample chamber and arranged to draw the sample continuously into the sample chamber at a predetermined substantially constant flowrate.

* * * * *